US008818524B2

(12) United States Patent
Hincapie Ordonez et al.

(10) Patent No.: US 8,818,524 B2
(45) Date of Patent: *Aug. 26, 2014

(54) METHOD FOR DETECTING VAGUS CAPTURE

(71) Applicant: Cardiac Pacemakers, Inc., St. Paul, MN (US)

(72) Inventors: Juan Gabriel Hincapie Ordonez, Maple Grove, MN (US); Stephen J. Hahn, Shoreview, MN (US); David J. Ternes, Roseville, MN (US); Shantha Arcot-Krishnamurthy, Vadnais Heights, MN (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/012,607

(22) Filed: Aug. 28, 2013

(65) Prior Publication Data

US 2013/0345591 A1 Dec. 26, 2013

Related U.S. Application Data

(63) Continuation of application No. 13/586,432, filed on Aug. 15, 2012, now Pat. No. 8,594,805.

(60) Provisional application No. 61/526,568, filed on Aug. 23, 2011.

(51) Int. Cl.
*A61N 1/00* (2006.01)

(52) U.S. Cl.
USPC .......................................................... 607/62

(58) Field of Classification Search
USPC .......................................................... 607/62
See application file for complete search history.

(56) References Cited

U.S. PATENT DOCUMENTS

| | | | |
|---|---|---|---|
| 4,114,627 | A | 9/1978 | Lewyn et al. |
| 5,161,529 | A | 11/1992 | Stotts et al. |
| 5,941,903 | A | 8/1999 | Zhu et al. |
| 6,427,085 | B1 | 7/2002 | Boon et al. |
| 6,600,954 | B2 | 7/2003 | Cohen et al. |
| 7,801,603 | B2 | 9/2010 | Westlund et al. |
| 7,840,280 | B2 | 11/2010 | Parnis et al. |

(Continued)

FOREIGN PATENT DOCUMENTS

WO    WO-2013028428 A1    2/2013

OTHER PUBLICATIONS

U.S. Appl. No. 13/586,43, Non Final Office Action mailed Apr. 12, 2013, 15 pgs.

(Continued)

*Primary Examiner* — Robert N Wieland
(74) *Attorney, Agent, or Firm* — Schwegman Lundberg & Woessner, P.A.

(57) ABSTRACT

Some embodiments provide a system for delivering neurostimulation. Some system embodiments comprise a lead configured to be implanted in the body, a stimulation output circuit configured to deliver neurostimulation pulses to the vagus nerve through the lead, an EMG sensing circuit configured to use the lead to sense EMG signals from laryngeal muscle activity, and an evoked muscular response detection circuit configured to use the EMG signals sensed by the EMG sensing circuit to detect evoked laryngeal muscle activity evoked by the neurostimulation pulse.

20 Claims, 24 Drawing Sheets

(56) References Cited

U.S. PATENT DOCUMENTS

| | | |
|---|---|---|
| 2006/0058854 A1 | 3/2006 | Abrams et al. |
| 2009/0054947 A1 | 2/2009 | Bourn et al. |
| 2010/0114221 A1 | 5/2010 | Krause et al. |
| 2010/0145221 A1 | 6/2010 | Brunnett et al. |
| 2010/0191311 A1* | 7/2010 | Scheiner et al. ............ 607/62 |
| 2011/0015704 A1 | 1/2011 | Ternes et al. |
| 2011/0313483 A1 | 12/2011 | Hincapie Ordonez et al. |
| 2013/0053926 A1 | 2/2013 | Hincapie Ordonez et al. |

OTHER PUBLICATIONS

U.S. Appl. No. 13/586,432, Response filed Jul. 11, 2013 to Non Final Office Action mailed Apr. 12, 2013, 11 pgs.

U.S. Appl. No. 13/586,432, Notice of Allowance mailed Jul. 26, 2013, 10 pgs.

International Application Serial No. PCT/US2012/050940, International Search Report mailed Dec. 13, 2012, 5 pgs.

International Application Serial No. PCT/US2012/050940, Written Opinion mailed Dec. 13, 2012, 7 pgs.

Ardesch, J. J, et al., "Vagus nerve stimulation for epilepsy activates the vocal folds maximally at therapeutic levels", Epilepsy Research, Elsevier Science Publishers, vol. 89, No. 2-3, (May 1, 2010), 227-231.

Castoro, M. A, et al., "Excitation properties of the right cervical vagus nerve in adult dogs", Exp Neurol., 227(1), (Jan. 2011), 62-8.

Ordelman, S. C, et al., "An indirect component in the evoked compound action potential of the vagal nerve", J Neural Eng., 7(6), (Dec. 2010), 066001 (9 pgs.).

Schneider, Rick, et al., "A new anchor electrode design for continuous neuromonitoring of the recurrent laryngeal nerve by vagal nerve stimulations", Langenbeck's Archives of Surgery, Springer, vol. 394. No. 5, (May 9, 2009), 903-910.

* cited by examiner

METHOD FOR DETECTING VAGUS CAPTURE

CLAIM OF PRIORITY

This application is a continuation of U.S. application Ser. No. 13/586,432, filed Aug. 15, 2012, which claims the benefit of priority under 35 U.S.C. §119(e) of Ordonez et al., U.S. Provisional Patent Application Ser. No. 61/526,568, entitled "SYSTEMS AND METHODS TO DETECT VAGUS CAPTURE", filed on Aug. 23, 2011, each of which is herein incorporated by reference in its entirety.

TECHNICAL FIELD

This application relates generally to medical devices and, more particularly, to systems, devices and methods for delivering neural stimulation.

BACKGROUND

Neural stimulation, such as vagus nerve stimulation, has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

SUMMARY

Some embodiments provide a method, comprising delivering neurostimulation pulses to the vagus nerve through an implanted lead, using the implanted lead to sense EMG signals from laryngeal muscle activity, and using sensed EMG signals to detect evoked laryngeal muscle activity evoked by the neurostimulation pulses, as recited in the claim.

Some embodiments provide a system for delivering neurostimulation. Some system embodiments comprise a lead configured to be implanted in the body, a stimulation output circuit configured to deliver neurostimulation pulses to the vagus nerve through the lead, an EMG sensing circuit configured to use the lead to sense EMG signals from laryngeal muscle activity, and an evoked muscular response detection circuit configured to use the EMG signals sensed by the EMG sensing circuit to detect evoked laryngeal muscle activity evoked by the neurostimulation pulses.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
FIG. 1 illustrates increasing vagal stimulation therapy (VST) intensity from the left side to the right side of the figure, and further illustrates intensity thresholds that elicit various physiological responses to VST.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent neurons convey impulses towards the central nervous system (CNS), and efferent neurons convey impulses away from the CNS.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intestine, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. Some embodiments of the present subject matter can be used to prophylactically or therapeutically treat various cardiovascular diseases by modulating autonomic tone. Neural stimulation to treat cardiovascular diseases is referred to herein as neurocardiac therapy (NCT). Vagal stimulation used to treat cardiovascular diseases may be termed either vagal stimulation therapy (VST) or NCT. However, VST may be delivered for non-cardiovascular diseases, and NCT may be delivered by stimulating a nerve other than the vagal nerve. Examples of cardiovascular diseases or conditions that may be treated using VST include hypertension, HF, and cardiac remodeling. These conditions are briefly described below.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Nerve cuffs may be used to stimulate the vagus nerve. Transvascularly stimulating the vagus nerve using electrodes in a blood vessel such as the internal jugular vein is less invasive. Another less invasive means for stimulating the vagus nerve includes stimulating the vagus nerve using electrodes placed proximate to the nerve within the carotid sheath. Verifying vagus nerve capture is desirable, particularly in non-cuff electrode arrangements. Verifying vagus nerve capture may also be relevant for automatic titration in both cuff and non-cuff electrode arrangements.

A branch of the vagus nerve is the recurrent laryngeal nerve, which innervates the laryngeal muscles. The vagus nerve is stimulated at a stimulation site more cranial than the position where the recurrent laryngeal nerve branches off of the vagus nerve. Stimulation that captures the vagus nerve at this stimulation site enhances efferent vagal nerve traffic from this position, propagating action potentials through the recurrent laryngeal nerve and causing laryngeal muscle activation. Various embodiments of the present subject matter deliver vagal stimulation to enhance efferent vagal nerve traffic, and detect activation of the laryngeal muscles to provide feedback to a physician during the implantation procedure, to provide feedback to a physician during physician follow-ups, or to provide feedback for auto-titration routines intermittently performed in an implanted device.

The present subject matter generally refers to therapeutic stimulation of the vagus nerve. VST may include stimulation to increase vagus nerve traffic, stimulation to block or reduce vagus nerve traffic, unidirectional stimulation of the vagus nerve (e.g. stimulation that significantly affects nerve traffic in the afferent direction but not the efferent direction, or stimulation that significantly affects nerve traffic in the efferent direction but not the afferent direction), or stimulation that is non-unidirectional (e.g. stimulation that significantly affects nerve traffic in both the afferent and efferent direction). Therefore, the VST delivered from the stimulation electrodes for the therapy may enhance efferent vagal nerve traffic after vagus nerve capture is verified or the therapy is titrated. However, the present subject matter may be used to verify vagus nerve capture, and then provide a VST that does not enhance efferent vagal nerve activity. For example, the device may be configured to block efferent vagal nerve activity or to deliver VST to unidirectionally enhance afferent vagus nerve activity after vagus nerve capture is verified. The parameters used to verify vagus nerve capture can be used to determine the appropriate VST parameters, whether the VST is configured to increase afferent or efferent nerve traffic either unidirectionally or non-unidirectionally, or whether the VST is configured to block or decrease efferent nerve traffic, afferent nerve traffic or both efferent and afferent nerve traffic.

The vagus nerve is a complex physiological structure with many neural pathways that are recruited at different stimulation thresholds. Various physiological responses to vagal stimulation are associated with various thresholds of VST intensity. For example, FIG. 1 illustrates increasing VST intensity from the left side to the right side of the figure, and further illustrates intensity thresholds that elicit various physiological responses to VST. VST causes a physiological response "A" at a lower intensity than an intensity at which VST causes a physiological response "B", which occurs at a lower VST intensity than an intensity at which VST causes a physiological response "C". Stated another way, VST triggers response "A" after reaching a certain level, triggers response "B" along with response "A" after reaching a higher intensity, and triggers response "C" along with responses "A" and "B" after reaching an even higher intensity.

Physiological responses at lower VST intensities have therapeutically-effective results for cardiovascular diseases such as HF. Lower VST intensities may also have therapeutically-effective results for other diseases. These responses mediate or provide pathways for these therapies. Examples of such responses that are beneficial for HF at the lower VST intensities include anti-inflammation, anti-sympathetic, and anti-apoptosis responses, and an increased nitric oxide (NO). Physiological responses at the higher VST intensities may not be desirable. Examples of responses to higher VST intensities that may reduce the ability of the patient to tolerate VST include, but are not limited to, reduced heart rate, prolonged AV conduction, vasodilation, and coughing. At least some of these responses may be desirable for some therapies but not desirable for other therapies. By way of example and not limitation, VST that reduces heart rate and or that prolongs AV conduction may be desirable to treat some cardiovascular diseases, but may not be desirable for other cardiovascular diseases. The intensity of the VST can be adjusted by adjusting parameter(s) of the stimulation signal. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal (e.g. a frequency of stimulation pulses), a stimulation burst frequency (e.g. a plurality of bursts delivered at a burst frequency for initiating bursts where each burst includes a plurality of pulses), a pulse width and/or a duty cycle. Typical vagal nerve stimulation may have a signal amplitude of above 0.1-10 mA and a frequency of about 1-50 Hz.

Figure 2:
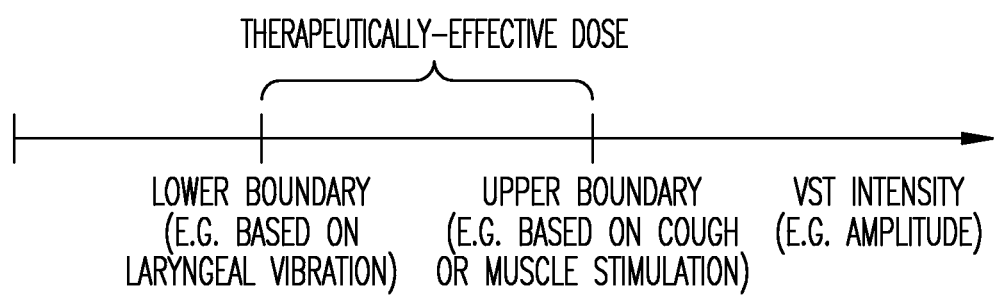
FIG. 2 illustrates increasing VST intensity from the left side to the right side of the figure, and further illustrates an intensity threshold for a laryngeal vibration response that can be used to determine capture and that can further be used as a lower boundary or to determine the lower boundary.

FIG. 2 illustrates increasing VST intensity from the left side to the right side of the figure, and further illustrates an intensity threshold for a laryngeal vibration response that can be used to determine capture and that can further be used as a lower boundary or to determine the lower boundary. A vagus nerve capture threshold can be set by confirming capture of the vagus nerve using laryngeal vibration. The stimulation parameters may be set based on the stimulation parameters that caused the laryngeal vibrations. For example, if the amplitude of the stimulation signal is increased to increase the VST intensity and if 1.0 mA caused laryngeal vibrations, then the pacing amplitude may be set to an offset value (x mA) above the laryngeal vibration threshold amplitude (e.g. 1 mA+x mA) or as a factor of the laryngeal vibration threshold (e.g. 1 mA*factor). Additionally, some embodiments may place an upper boundary on the VST. The upper boundary may be based on a detected undesired response to the stimulation, such as cough or undesired muscle stimulation.

Embodiments of the present subject matter use electromyogram (EMG) sensor(s) to detect activity of the laryngeal muscles. Some embodiments use multiple sensor strategies, along with the EMG sensor(s), to confirm vagal nerve stimulation. For example, an accelerometer could be used in the same time window and operating at a different bandwidth.

Figure 3:
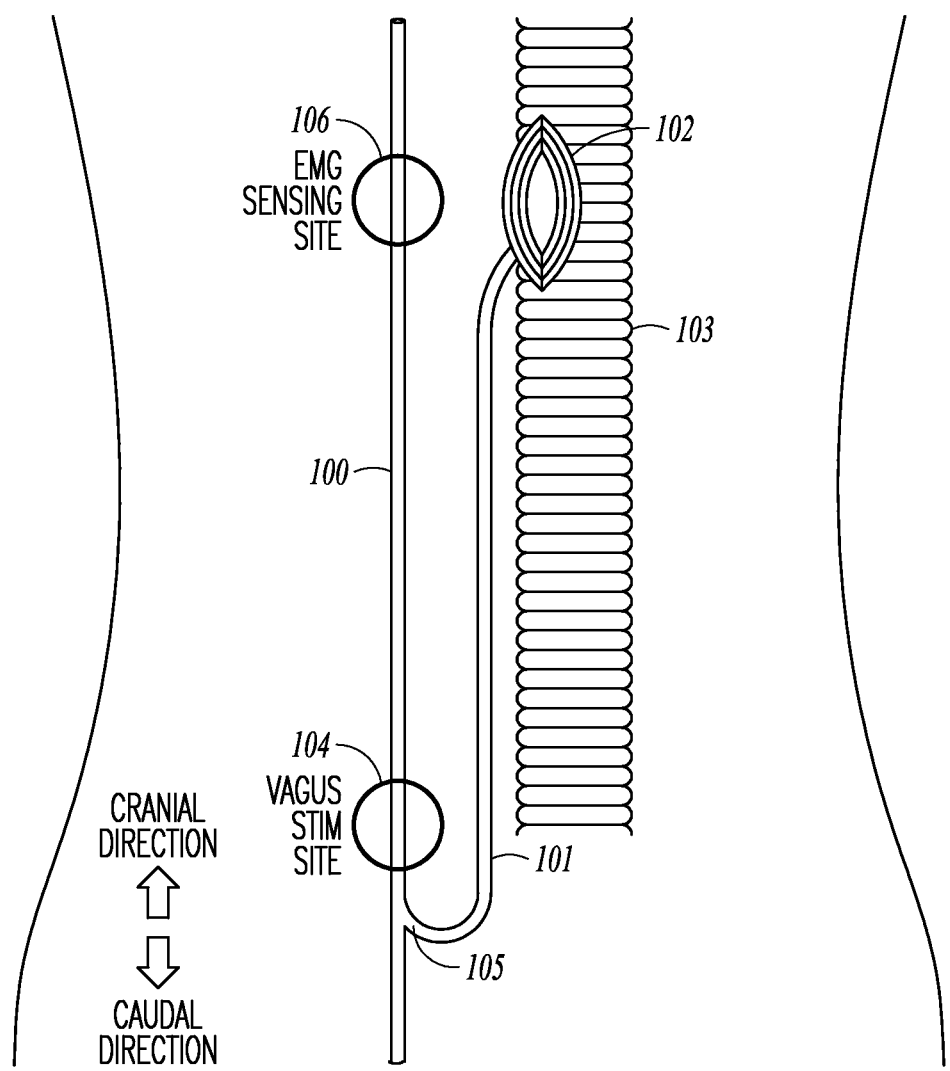
FIG. 3 generally illustrates a right vagus nerve and a recurrent laryngeal nerve branching off of the right vagus nerve to innervate the laryngeal muscles near the trachea.

FIG. 3 generally illustrates a right vagus nerve 100 and a recurrent laryngeal nerve 101 branching off of the right vagus nerve to innervate the laryngeal muscles 102 near the trachea 103. There is also a left vagus nerve (not illustrated) and a recurrent laryngeal nerve (not illustrated) branching off of the left vagus nerve to innervate the laryngeal muscles near the trachea. The ability to verify capture of a vagus nerve through EMG sensing of activity in laryngeal muscles may be used with right and/or left vagus nerve stimulation. The recurrent laryngeal nerve branches off the vagus nerve at a position caudal to the laryngeal muscles, and then loops back cranially to innervate the laryngeal muscles. This loop is a relatively lengthy neural pathway that provides latency between the time of a vagus nerve stimulation pulse and the time of the activation of the laryngeal muscles. Because of this latency, the laryngeal activation can be measured by EMG sensors after the pulse without being blunted by the stimulation artifact. Further, the loop provides options for adjusting the distance between the vagus nerve stimulation site and the laryngeal muscles. For example, in the embodiment illustrated in FIG. 3, the stimulation electrodes may be placed to stimulate the vagus nerve at stimulation site 104 relatively near the point 105 where the recurrent laryngeal nerve branches off the vagus nerve, and the EMG sensor(s) can be positioned along the vagus nerve at EMG sensing site 106 proximate to the laryngeal muscles to improve detection of activity in the laryngeal muscles and reduce the potential of interference from stimulation pulses. The stimulation electrodes and EMG sensor(s) may be on the same lead.

The vagus nerve includes A-fibers, B-fibers, and C-fibers. A-fibers are about 5-20 µm in diameter and conduct neural responses at a rate of approximately 0.08-0.33 ms/cm. B-fibers are about 1-5 µm in diameter and conduct neural responses at a rate of approximately 0.33-1.67 ms/cm. C-fibers are about 0.2-1.5 µm in diameter and conduct neural responses at a rate of approximately 8.16-22.36 ms/cm. U.S. application Ser. No. 13/156,879, filed Jun. 9, 2011 and entitled "Methods and Apparatus for Controlling Neurostimulation Using Evoked Responses" is incorporated herein by reference in its entirety. The larger fibers have a lower stimulation threshold than smaller fibers. Thus, the A-fibers have the lowest stimulation threshold. A-fibers of the vagus nerve are also somatic fibers, some of which branch off into the recurrent laryngeal nerve that innervate the muscles of the larynx.

Assuming a 0.17 ms/cm conduction rate for a 10 µm A-fiber that innervates the muscles of the larynx and assuming 50-60 cm of travel distance from the stimulated location of the vagus nerve into the recurrent laryngeal nerve and back up to the laryngeal muscles, the muscles of the larynx will activate about 8.33-10 ms after the vagus nerve is stimulated. Thus, the response of the laryngeal muscles to vagal nerve stimulation has a relatively long latency because of the relatively long travel distance. The actual distance from the stimulation site to the laryngeal muscles will depend on the location of the stimulation site and the specific anatomy of the patient. For example, taller people with longer necks may have longer recurrent laryngeal nerves. Patient specific templates may be developed to account for the specific anatomical differences in the patient.

Figure 4A:
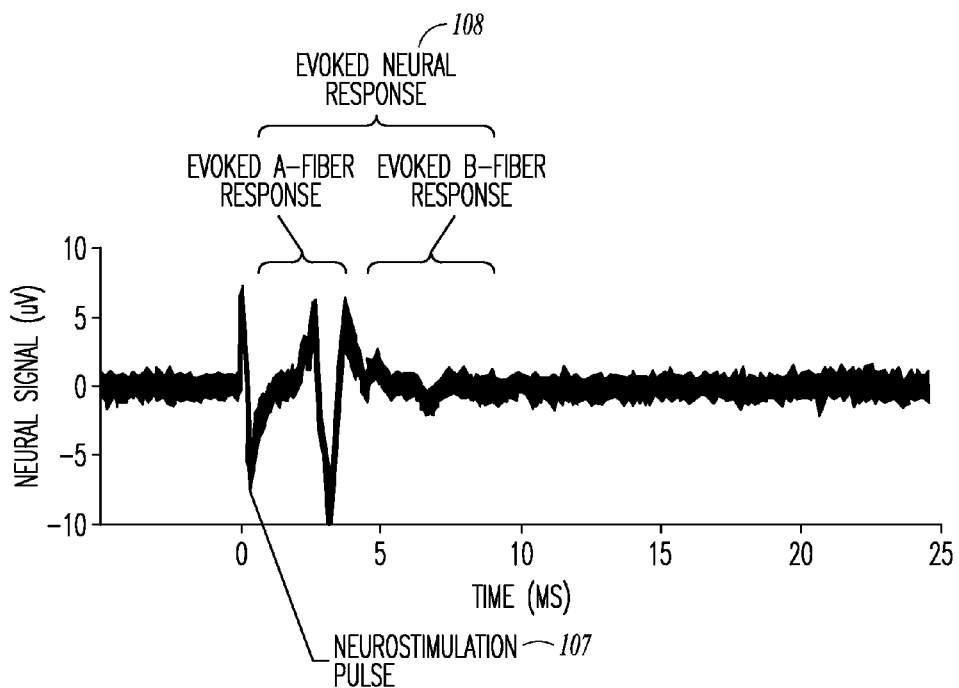
FIGS. 4A and 4B illustrate the latency of the laryngeal muscle activity to a vagus nerve pulse, comparing an ENG signal (FIG. 4A) to an EMG signal (FIG. 4B).
Figure 4B:
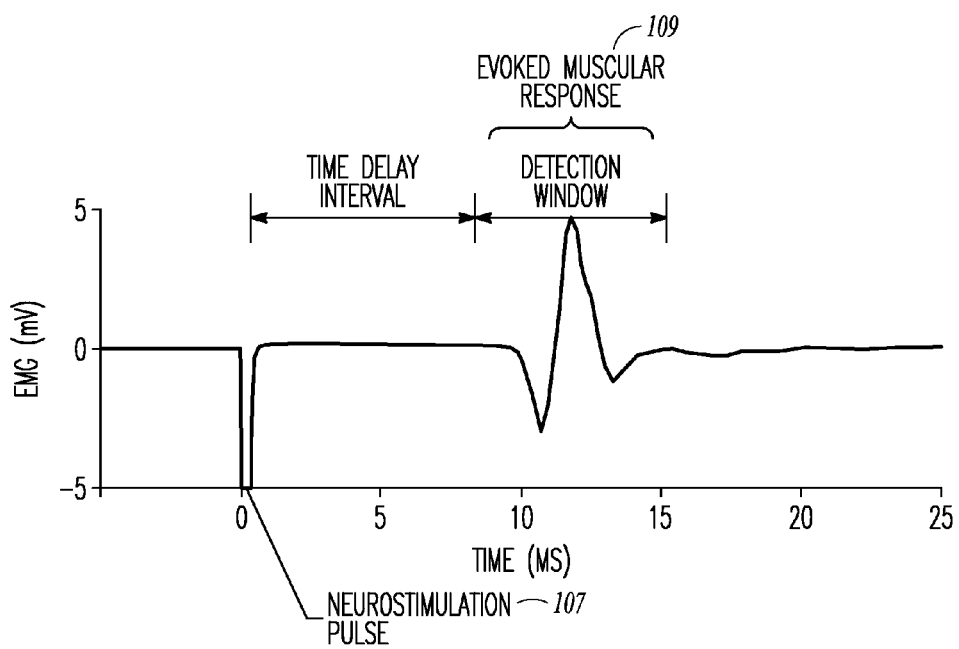

FIGS. 4A and 4B illustrate the latency of the laryngeal muscle activity to a vagus nerve pulse, comparing an ENG signal (FIG. 4A) to an EMG signal (FIG. 4B). A vagus nerve pulse 107 occurs at Time 0. An evoked neural response 108, including both an A-fiber response and a B-fiber response, to the pulse is detected by vagus ENG sensors (top) and an EMG showing the response of the laryngeal muscles to the pulse is detected by EMG sensor(s). As illustrated, the activity of the laryngeal muscles is about 10 ms after the delivery of the vagus nerve pulse.

Some embodiments use multiple lead configurations and recording vectors. For example, some embodiments use a bipolar electrode arrangement using a multi-polar lead such as a quad polar lead. Some embodiments use a tripolar electrode arrangement using three electrodes on the lead, which may improve stimulation artifact control. Some embodiments use a monopolar electrode arrangement, where an electrode on the pulse generator and an electrode on the lead provide the stimulation vector. Some embodiments deliver bilateral vagal nerve stimulation, using a right lead positioned to stimulate the right vagus nerve and a left lead positioned to stimulate the left vagus nerve. When the right vagus nerve is stimulated, the left lead is used to sense laryngeal activity; and when the left vagus nerve is stimulated, the right lead is used to sense laryngeal activity.

Figure 5:
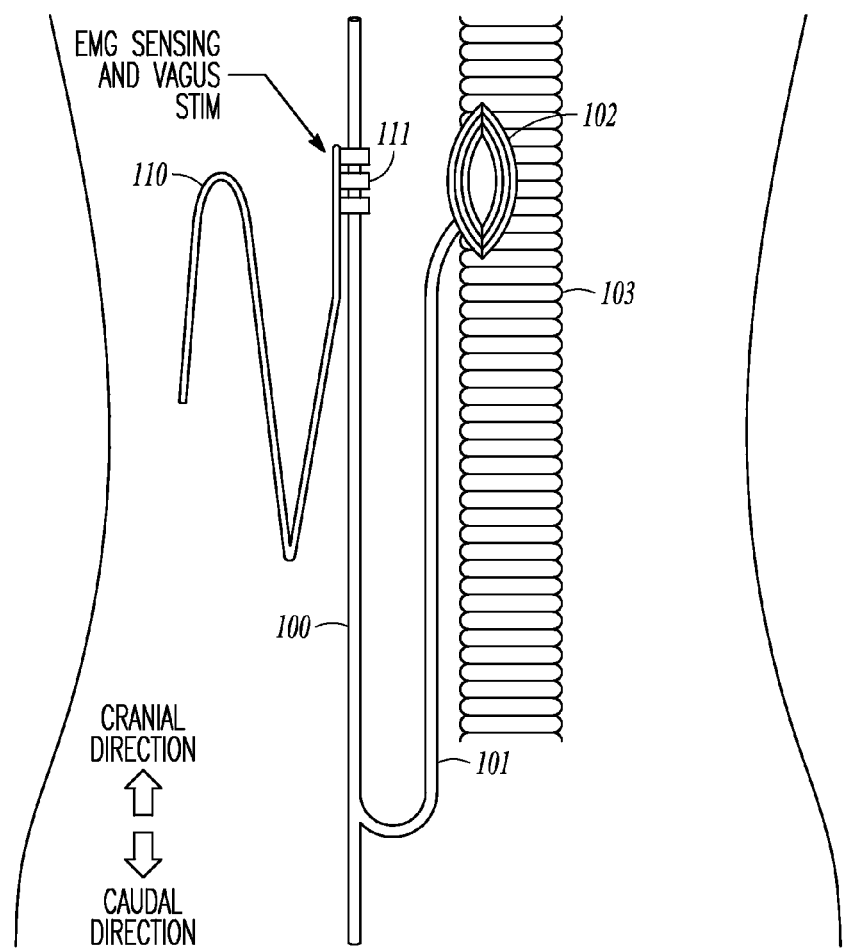
FIGS. 5-8 illustrate various embodiments for positioning electrodes to stimulate the vagus nerve and record activity of laryngeal muscles using an EMG signal.

FIGS. 5-8 illustrate various embodiments for positioning electrodes to stimulate the vagus nerve and record activity of laryngeal muscles using an EMG signal. FIG. 5 illustrates a vagus nerve 100 and a recurrent laryngeal nerve 101 branching off of the vagus nerve to innervate the laryngeal muscles 102 near the trachea 103, and further illustrate a nerve cuff embodiment. A lead 110 is attached to the vagus nerve 100 by a nerve cuff 111, and the nerve cuff includes electrodes used to stimulate the vagus nerve and to record EMG signals representing activity of the laryngeal muscles. If the vagus nerve is being captured, the pulses from the nerve cuff 111 stimulate efferent nerve activity in the vagal nerve through the recurrent nerve to the laryngeal muscles. In some embodiments, the neural stimulation electrodes are used to record the EMG signals. The same electrodes used to stimulate the vagus nerve may be used to record EMG activity. Some embodiments implement an autocapture routine that blank the sensing during the stimulation and then sense for an EMG artifact caused by an evoked response of the laryngeal muscles to the vagus nerve stimulation. In some embodiments, the nerve cuff includes a first set of electrodes used to stimulate the vagus nerve and includes a second set of electrodes used to record the EMG signal. In some embodiments, the first and second sets of electrodes are exclusive of each other. In some embodiments, the first and second sets of electrodes include at least one common electrode used to both stimulate the vagus nerve and record EMG activity.

Figure 6A:
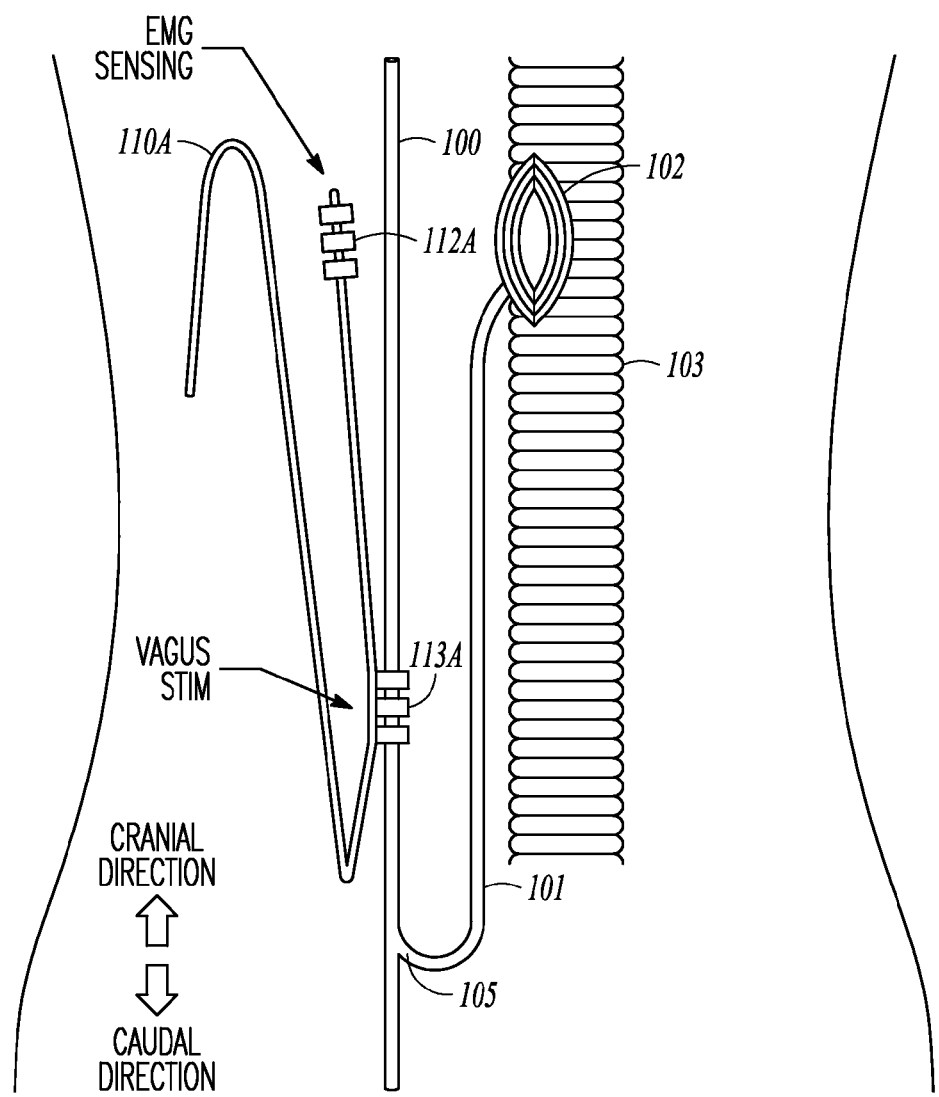

FIG. 6A illustrates a nerve cuff embodiment with recording electrodes 112A and with stimulation electrodes 113A positioned in a more caudal position closer to a position 105 where the recurrent laryngeal nerve branches from the vagus nerve 100. The position of the stimulation electrodes 113A at the stimulation site is cranial to the location where the recurrent laryngeal nerve branches from the vagus nerve. The stimulation electrodes 113A and the recording electrodes 112A are on a lead 110A. The illustrated stimulation electrodes 113A are part of a nerve cuff. The recording electrodes 112A are on a distal end of the lead 110A. If the vagus nerve is being captured, the pulses from the nerve cuff stimulate efferent nerve activity in the vagal nerve through the recurrent nerve to the laryngeal muscles, and the recording electrodes are capable of detecting activity in the laryngeal muscles caused by the vagus nerve pulses. The lower (more caudal) position of the stimulation electrodes places more distance between the stimulation electrodes and recording electrodes, which is believed to reduce a risk of interference.

Figure 6B:
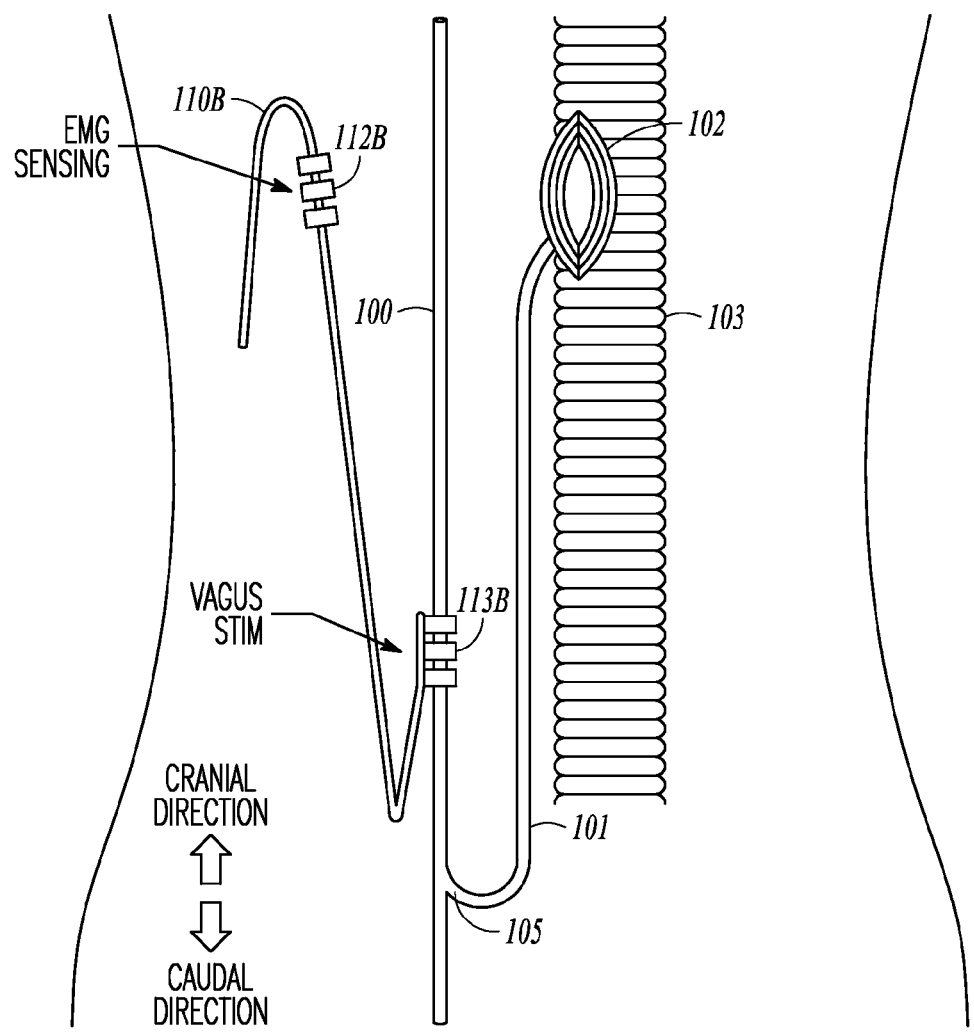

FIG. 6B illustrates a nerve cuff embodiment with recording electrodes 112B and with stimulation electrodes 113B positioned in a more caudal position closer to a position 105 where the recurrent laryngeal nerve branches from the vagus nerve. The position of the stimulation electrodes 113B at the stimulation site is cranial to the location where the recurrent laryngeal nerve branches from the vagus nerve. The stimulation electrodes 113B and the recording electrodes 112B are on a lead 110B. The illustrated stimulation electrodes 113A are part of a nerve cuff. The stimulation electrodes 113B are on a distal end of the lead 110B. If the vagus nerve is being captured, the pulses from the nerve cuff stimulate efferent nerve activity in the vagal nerve through the recurrent nerve to the laryngeal muscles, and the recording electrodes are capable of detecting activity in the laryngeal muscles caused by the vagus nerve pulses. The lower (more caudal) position of the stimulation electrodes places more distance between the stimulation electrodes and recording electrodes, which is believed to reduce a risk of interference.

Figure 7:
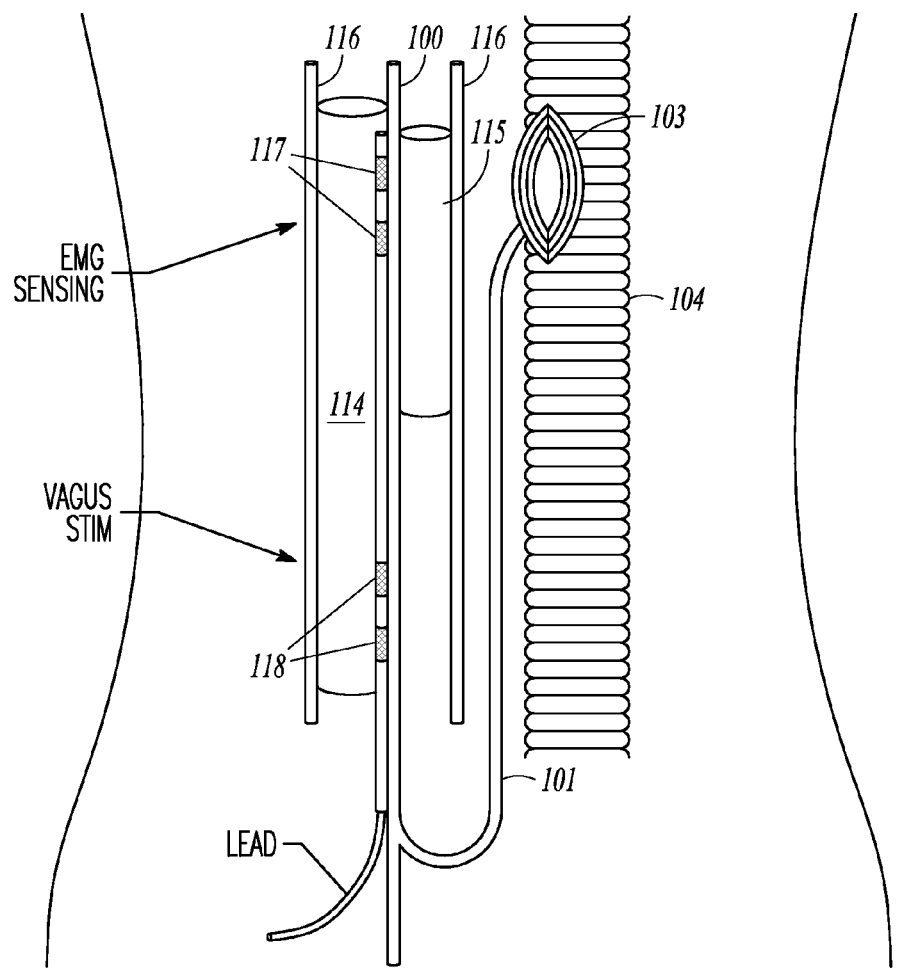

FIG. 7 illustrates an intrasheath lead embodiment, in which the stimulation and recording electrodes are placed within a carotid sheath 116 proximate to the vagus nerve. The carotid sheath 116 refers to the fibrous connective tissue that surrounds the carotid artery and related structures in the neck. The carotid sheath 116 contains the carotid arteries, the internal jugular vein, and the vagus nerve. The glossopharyngeal nerve and accessory nerve courses in the upper part of the carotid sheath 116, and the hypoglossal nerve passes through or near the carotid sheath 116. The internal jugular vein 114, the vagus nerve 100 and the carotid artery 115 are physiological structures found within the carotid sheath 116. The recording electrodes 117 are placed within the carotid sheath 116 approximately near the level of the laryngeal muscles, and the stimulation electrodes 118 are placed more caudally near the vagus nerve but still cranial to the location where the recurrent laryngeal nerve branches from the vagus nerve. If the vagus nerve is being captured, the pulses from the nerve cuff stimulate efferent nerve activity in the vagal nerve through the recurrent nerve to the laryngeal muscles, and the recording electrodes are capable of detecting activity in the laryngeal muscles. The recording electrodes and stimulation electrodes are on the same lead and are fed into the carotid sheath with the lead.

Figure 8:
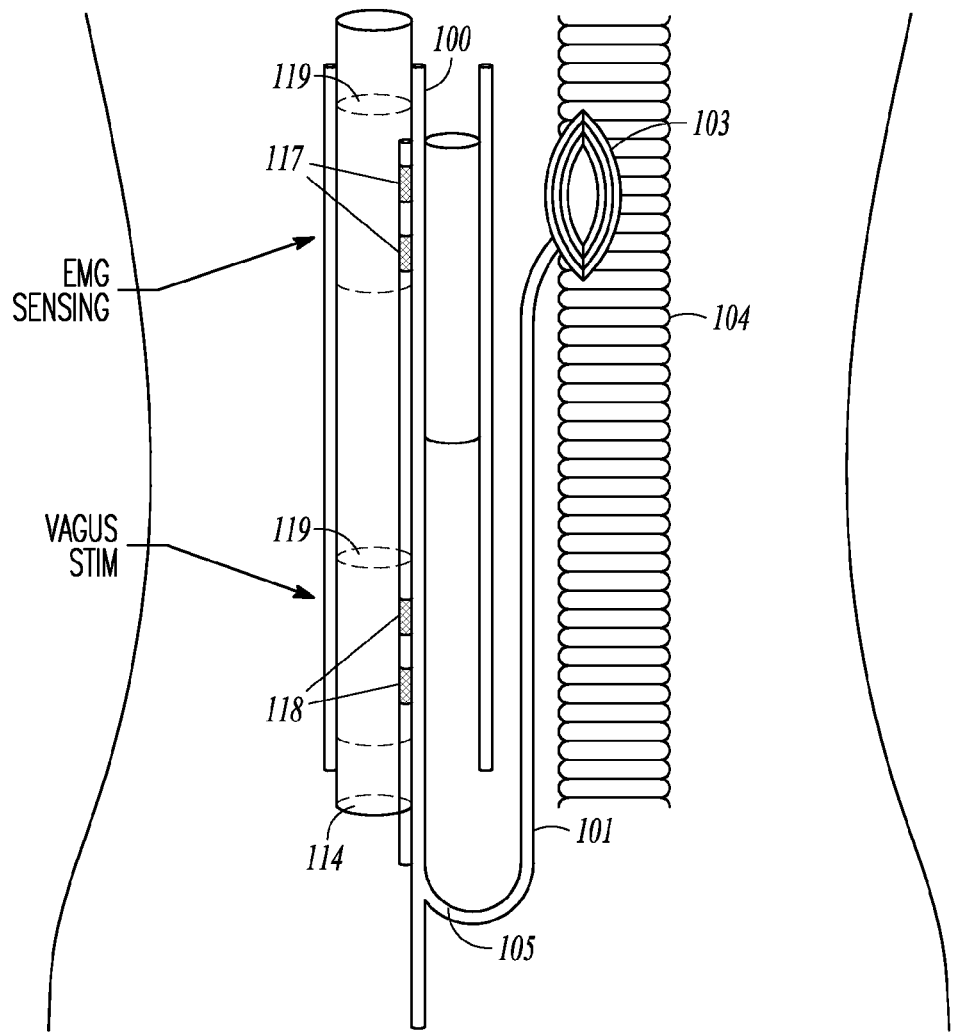

FIG. 8 illustrates an intravascular embodiment, in which the stimulation and recording electrodes are placed within an internal jugular vein proximate to the vagus nerve. The recording electrodes 117 are placed within the internal jugular vein 114 approximately near the level of the laryngeal muscles 103, and the stimulation electrodes 118 are placed more caudally near the vagus nerve 100 but still cranial to the location 105 where the recurrent laryngeal nerve 101 branches from the vagus nerve 100. If capturing the vagus nerve, the pulses from the nerve cuff stimulate efferent nerve activity in the vagal nerve through the recurrent nerve to the laryngeal muscles, and the recording electrodes are capable of detecting activity in the laryngeal muscles. The lead is fixed within the vessel using an anchoring system, such as an expandable stent-like device(s) 119. The anchoring system can function to maintain the position of the electrodes against a vessel wall proximate to the vagus nerve, and at the desired cervical region to stimulate the vagus nerve and sense the resulting activity of the laryngeal muscles.

Figure 9:
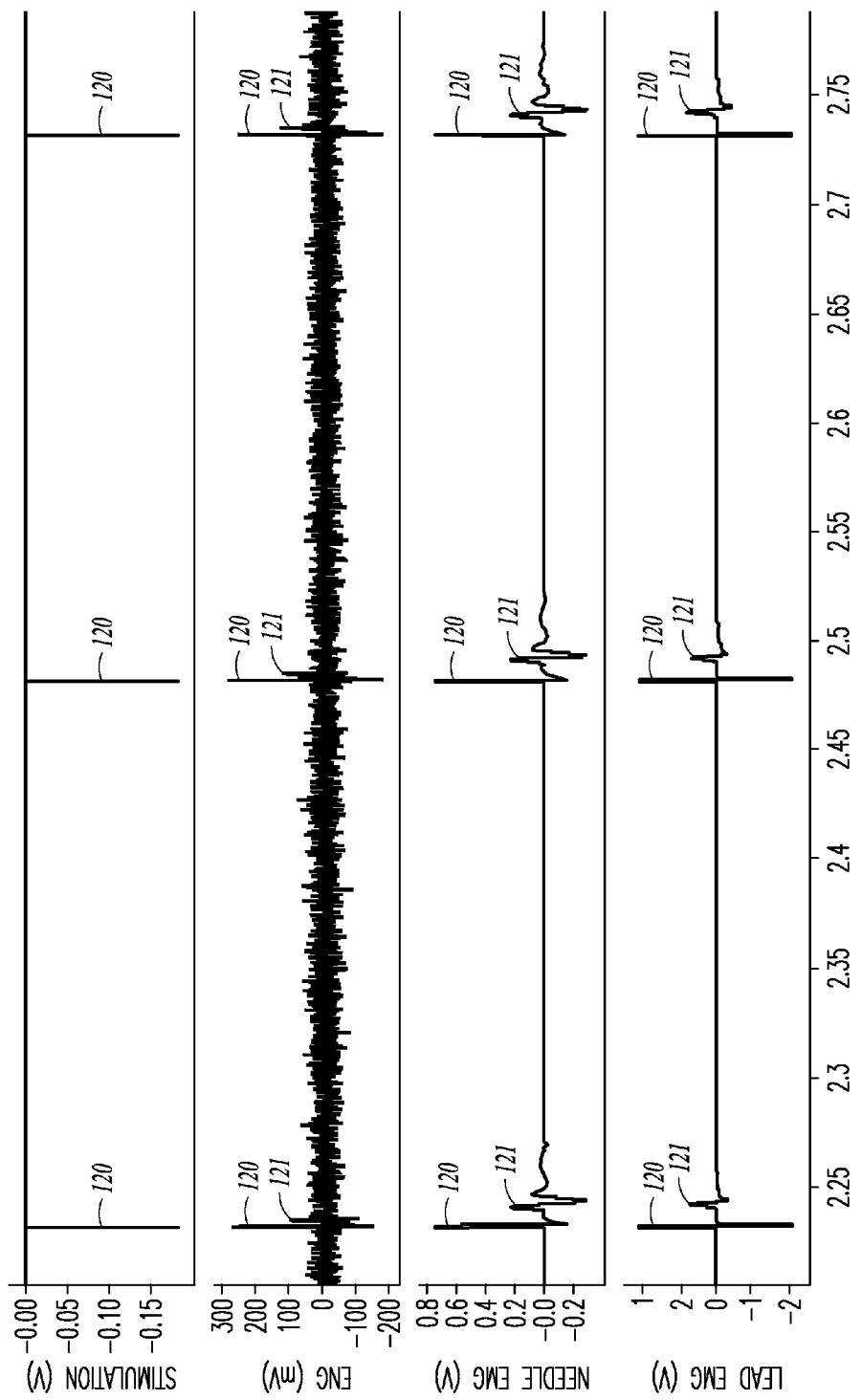
FIGS. 9-10 illustrate results of an experiment in which the vagus nerve was stimulated, an ENG signal reflecting vagal nerve traffic was recorded, and EMG signals of laryngeal muscle activity was recorded using a needle EMG sensor and a lead EMG sensor.
Figure 10:
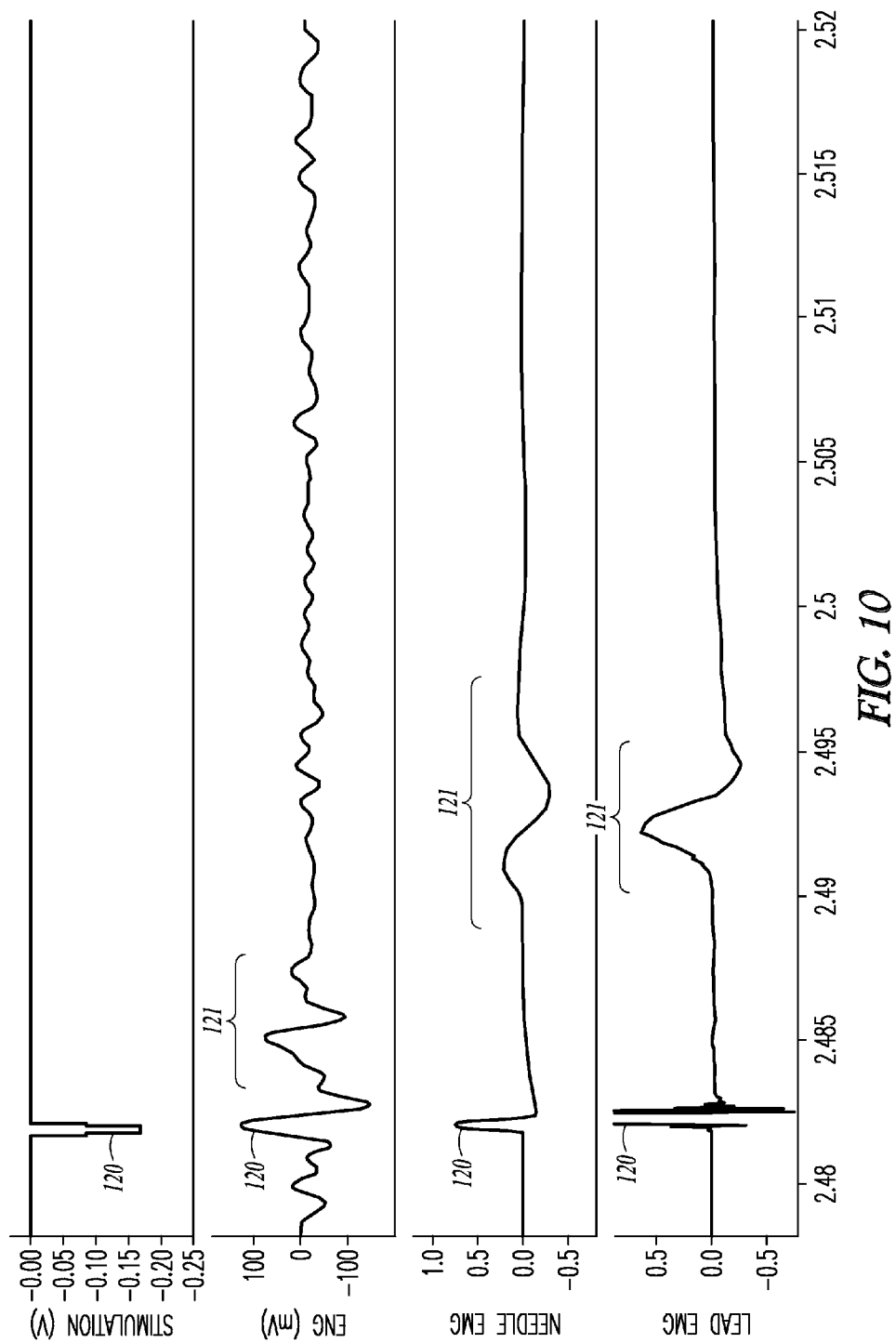

FIGS. 9-10 illustrate results of an experiment in which the vagus nerve was stimulated, an ENG signal reflecting vagal nerve traffic was recorded using a nerve cuff around the vagus nerve, and EMG signals of laryngeal muscle activity were recorded using a needle EMG sensor percutaneously placed on the larynx muscles and a lead EMG sensor implanted in the carotid sheath next to the vagus nerve. Stimulation and lead EMG recordings were done from the same multi-polar lead implanted in the carotid sheath right next to the vagus nerve. The ENG and EMG signals show a representation of the pulse 120 and a response 121 to the pulse 120. FIG. 9 illustrates three neural stimulation pulses, and FIG. 10 is a closer view of a single pulse. As illustrated in the figures, the EMG signals are related to the ENG signal, albeit delayed by the latency that it takes to propagate action potentials through the vagus and recurrent laryngeal nerve, indicating that the EMG of laryngeal muscle activity is a reliable indicator of vagus nerve capture. Furthermore, the lead-based EMG sensor corresponds closely to the needle EMG sensor, indicating that the lead-based EMG sensor is also a reliable indicator of the laryngeal nerve activity and thus a reliable indicator of vagus nerve capture.

A capacitive double layer of charge forms when stimulus pulse is delivered after-potential or polarization. A recharge pulse can be delivered to remove this charge. However, the recording electrodes are used to sense an EMG signal from the laryngeal muscles in a sensing window approximately 10 ms after the vagus nerve stimulation pulse. The exact timing of the sensing window may depend on patient-specific anatomy and the position of the stimulation electrodes. Various embodiments provide a recharge after a stimulation pulse without interfering with the sensing of the laryngeal muscles within the sensing window.

Figure 11A:
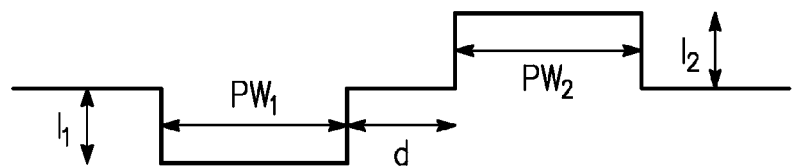
FIGS. 11A-11B illustrate active and passive recharge phases, such as may be used in various embodiments.

According to an embodiment, an active recharge phase is used to complete the recharge before a sensing window for sensing laryngeal activity using the EMG sensors. For example, a cathodic stimulus phase is followed by an active anodic stimulus recharge phase that completes before the sensing window. In an embodiment, the recharge pulse is equal in amplitude ($I_1 \approx I_2$) and pulse width ($PW_1 \approx PW_2$) to the cathodic stimulus phase, but opposite polarity, such as is generally illustrated in FIG. 11A.

Figure 11B:
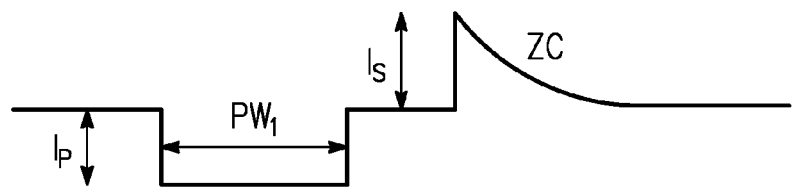

According to an embodiment, a passive recharge phase is stopped to provide a window for sensing laryngeal activity using the EMG sensors, and then resumed after the window to finish the recharge phase. For example, a cathodic stimulus phase is followed by a passive anodic stimulate recharge phase. A passive recharge phase is generally illustrated in FIG. 11B by the exponential waveform following the stimulation pulse PW and a delay. The recharge phase is stopped, if necessary, to provide a sensing window for a period of time when the laryngeal activity is expected. After the sensing window is completed, the passive anodic stimulus recharge phase is resumed and completed.

According to an embodiment, the EMG sensors are cable of sensing amplitudes within an approximate range of 0 to 500 μV, and have a bandwidth with an approximate range of 10-200 Hz. However, the present subject matter is not limited to a particular range of amplitudes or bandwidth. The detection can be performed by comparing parameter(s) from the sensed signal to a template. In some embodiments, the implanting physician creates the template after implanting the device. In some embodiments, a physician creates the template during a follow-up visit. In creating the template, the EMG signal is monitored for a signal deflection to flag the event as a vagal nerve capture event. A number of vagal nerve capture events can be averaged or otherwise processed to provide the template, and to provide the sensing window timing for sensing laryngeal muscle activity after a vagus stimulation pulse. Signal averaging strategies can be used to demonstrate that the majority of pulses capture the vagus nerve. It is not necessary to demonstrate that an isolated pulse produced detectable activity in the laryngeal muscles.

According to some embodiment the sense amplifiers are blanked during the stimulus pulse. The gain and filter characteristics of the amplifiers are appropriate to detect the small signal representing the EMG of active laryngeal muscles. Some embodiments calibrate the sensors for each patient as amplitudes and timing may vary slightly because of implant location, neck length, and the like.

Signal processing is expected to be able to distinguish activation of laryngeal muscles from other muscle activity (e.g. neck motion). However, some embodiments of the laryngeal activity sensing are performed when the patient is still to prevent interference from other muscles. Patient movement is not an issue during an implantation procedure, and the patient may be instructed to lie still during a follow-up exam. In an implanted device embodiment configured to automatically perform the capture detection, the device may be configured to sense activity or motion or voice, and to disable the capture detection routine or otherwise provide context for recording EMG signals when the activity or motion or voice is above a threshold level.

Various embodiments use capture detection to augment a stimulation dose in the ambulatory setting. For example, a threshold capture routine can be performed for the ambulatory patient. The routine may be triggered by a physician, by a patient, or automatically based on a schedule, a period of time, or a sensed activity or event. The threshold may change over time because of lead migration, changes in the electrode-tissue interface, and neurological habituation to the stimulation signal, for example. The dose of the stimulation can be increased to account for the change in the stimulation threshold.

Various embodiments associate EMG strength to B-fiber capture and therapy delivery, such as described in U.S. application Ser. No. 13/156,879, filed Jun. 9, 2011 and entitled "Methods and Apparatus for Controlling Neurostimulation Using Evoked Responses", which is incorporated herein by reference in its entirety. It is believed that an approximately constant relationship can be identified between the stimulation threshold for capturing the A-fibers and the stimulation threshold for effectively modulating a target physiological function through capturing the B-fibers. The stimulation intensity is a minimum stimulation intensity required to activate laryngeal muscles. Once an initial stimulation threshold providing for the initial evoked muscular response is determined, the stimulation intensity for therapeutically stimulating B-fibers is set to a level that is determined by using the initial stimulation threshold and the identified approximately constant relationship. The initial evoked muscular response is the evoked muscular responses that start to become detectable as the stimulation intensity increases from a low initial level. The initial stimulation threshold is the stimulation intensity that produces the initial evoked muscular response. In one embodiment, the approximately constant relationship is quantitatively established using a patient population. The stimulation intensity for a vagus nerve stimulation therapy applied to the patient is then set using the initial stimulation threshold and the established approximately constant relationship.

The titration and capture detection routines can be triggered manually by a physician, triggered manually by a patient, or triggered automatically according to a programmed schedule or according to a time interval or according to a detected event. A titration can be triggered if it is determined that the stimulation is not capturing the vagus nerve.

To confirm capture of the vagus nerve, a device embodiment switches between normal and titration modes and switches between normal and confirmation modes. Titration has a higher priority than confirmation which has higher priority than normal mode. Performing titration/confirmation can be gated or aborted or blocked or delayed by a detected event or sensed context. For example, titration/confirmation can be gated or aborted or blocked or delayed by detecting an arrhythmia, a posture sensor value, a sleep sensor value, an activity sensor value, detected apnea or detected irregular breathing.

Titration, as used herein, refers to the process of adjusting the dose of the stimulation, ultimately to a level that is therapeutically or prophylactically effective. The titration procedure may occur during an implantation procedure, or during a follow-up clinical visit, or while a patient is ambulatory away from the clinical setting. The titration may be physician-controlled or automatically-controlled based on device programming. The dose includes an amount or intensity of the neural stimulation at a given time frame, and also includes the number of times the neural stimulation is delivered over a period of time. The intensity of the neural stimulation may be adjusted by adjusting parameters such as amplitude, duty cycle, duration, and or frequency of the neural stimulation, or the number of neural stimulation events that occur over a period of time.

Figure 12:
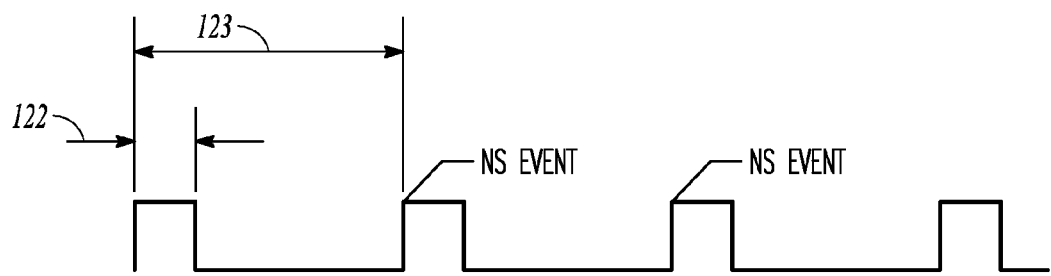
FIG. 12 illustrates a representation of intermittent neural stimulation (INS).

FIG. 12 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 122) is delivered, and intervals of stimulation being OFF, when no stimulation pulses are delivered. Thus, for example, some embodiments deliver a plurality of monophasic or biphasic pulses within a neural stimulation burst illustrated in FIG. 12. Pulses delivered within a burst 122 may be delivered at a pulse frequency. These pulses also have an amplitude. Both the pulse frequency and the pulse amplitude affect the dose of the neural stimulation therapy. The duration of the stimulation ON interval is sometimes referred to as the stimulation duration or burst duration. The burst duration also affects the dose of the neural stimulation therapy. The start of a stimulation ON interval is a temporal reference point NS Event. The time interval between successive NS Events is the INS Interval, which is sometimes referred to as the stimulation period or burst period 123. The burst period 123 or the number of neural stimulation events that occur over a time period also affect the dose of the neural stimulation. For an application of neural stimulation to be intermittent, the stimulation duration (i.e., ON interval) is less than the stimulation period (i.e., INS Interval) when the neural stimulation is being applied. The duration of the OFF intervals of INS are determined by the durations of the ON interval and the INS Interval. The duration of the ON interval relative to the INS Interval (e.g., expressed as a ratio) is sometimes referred to as the duty cycle of the INS.

Figure 14:
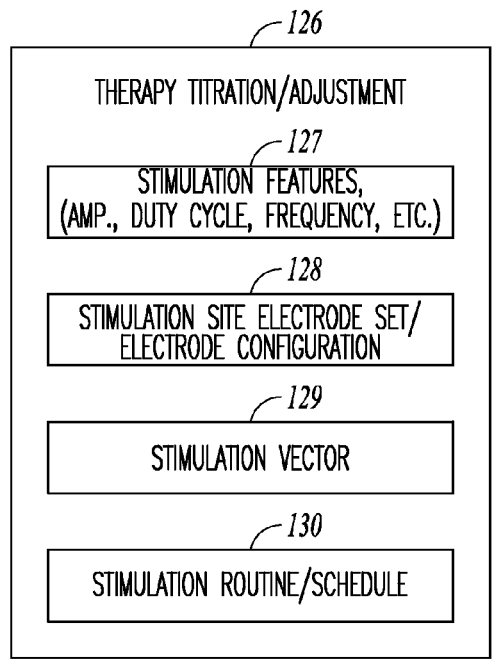
FIG. 14 illustrates an embodiment of a therapy titration module.

A physician or clinician may control the adjustment of one or more neural stimulation parameters to control the stimulation intensity. For example, during an implantation procedure in which stimulation electrodes are implanted near a vagus nerve, the physician or clinician may adjust stimulation parameter(s) to adjust the stimulation intensity to appropriately position the electrodes and program the stimulation to provide threshold stimulation of the neural target that provides a desired physiological effect. A desired physiological effect, according to various embodiments, is laryngeal vibrations caused by the stimulation of the vagus nerve cranially to the position where the laryngeal nerve branches from the vagus nerve. The physician or clinician may re-program an implantable neural stimulator during a follow-up visit, to account for migration of the electrodes, changes in impedance in the electrode/tissue interface, and the like. During the follow-up visit, the physician or clinician may control the adjustment of one or more neural stimulation parameters to control the stimulation intensity to determine a neural stimulation intensity that provides the desired physiological response. The titration routine can be an automatic process for an implantable neural stimulation device implanted in an ambulatory patient, such as generally illustrated in FIG. 14. The automatic titration routine can be manually triggered by a signal from a patient or by the physician or clinician. The automatic titration routine can be automatically triggered by a programming schedule or by a sensed event.

Figure 13:
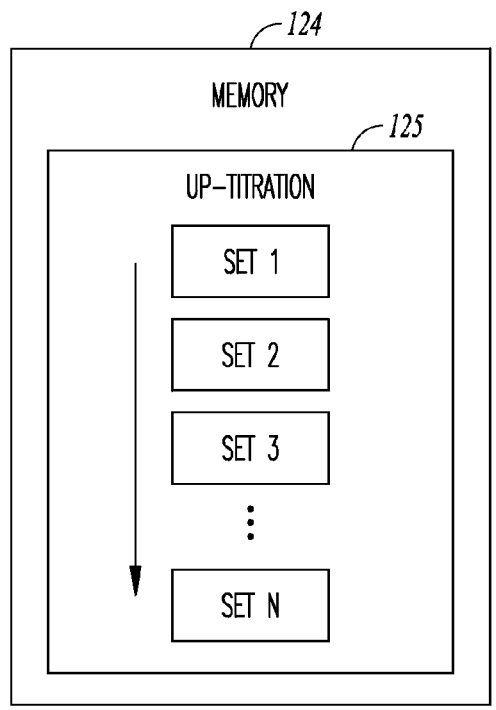
FIG. 13 illustrates a memory, according to various embodiments, that includes instructions operable on by stimulation control circuitry to control an up-titration routine by progressively stepping up through defined parameter sets where each set incrementally changes the stimulation dose or intensity of the stimulation therapy, according to various embodiments.

FIG. 13 illustrates a memory 124, according to various embodiments, that includes instructions 125, operable on by the stimulation control circuitry, to control an up-titration routine by progressively stepping up through defined parameter sets (e.g. parameter set 1 through parameter set N), where each set incrementally changes (increases or decreases) the stimulation dose or intensity of the stimulation therapy. This memory may be illustrated as part of a therapy titration/adjustment module 126 in FIG. 14 which may function as a parameter adjuster discussed below. The memory may include a plurality of neural stimulation parameter sets, where each set includes a unique combination of parameter values for the neural stimulation and wherein each unique combination of parameter values is defined to provide neural stimulation therapy at an intensity level. The instructions include instructions for stepping through the plurality of neural stimulation parameter sets according to a schedule to change (increase or decrease) the intensity of the therapy until the therapy is at the desired long term intensity. Various embodiments provide a neural stimulation routine that automatically finds the desirable combination of therapy parameters (e.g. amplitude, pulse width, duty cycle) that provides a desired therapy intensity level.

FIG. 14 illustrates an embodiment of a therapy titration module 126, which may also be referred to as a therapy adjustment module. According to various embodiments, the stimulation control circuit is adapted to set or adjust any one or any combination of stimulation features 127. Examples of stimulation features include the amplitude, pulse width, duty cycle and frequency of the stimulation signal. Some embodiments of the stimulation output circuit are adapted to generate a stimulation signal with a predetermined amplitude, pulse width, duty cycle and frequency and are further adapted to respond to a control signal from the controller to modify at least one of the amplitude, pulse width, duty cycle and frequency.

The therapy titration module 126, also referred to as a therapy adjustment module, can be programmed to change an electrode set or electrode configuration or to change stimulation sites 128, such as changing the stimulation electrodes used for a neural target or changing the neural targets for the neural stimulation. For example, different electrodes can be used to stimulate a neural target, and different electrodes can be used to stimulate different neural targets. A desirably low stimulation threshold for a neural target may be determined using different electrode sets/configurations for stimulating that neural target. Different neural targets can include different neural pathways such as the right and left vagus nerves. Different neural targets may include different positions along a neural pathway (e.g. more caudal or more cranial targets along a cervical vagus nerve). The neural stimulation delivered to confirm capture of the vagus nerve may be but need not be the same stimulation as delivered during the VST. For example, the VST may include stimulation to stimulate neural traffic or stimulation to inhibit neural traffic. Thus, stimulation to evoke a sympathetic response can involve inhibition of the parasympathetic traffic in the vagus nerve, and stimulation to evoke a parasympathetic response can involve stimulation of the parasympathetic traffic in the vagus nerve.

The therapy titration module 126 can be programmed to change stimulation vectors 129. Vectors can include stimulation vectors between electrodes, or stimulation vectors for transducers. For example, the stimulation vector between two electrodes can be reversed. More complicated combinations of electrodes can be used to provide more potential stimulation vectors between or among electrodes.

The therapy titration module 126 can be programmed to control the neural stimulation according to stimulation instructions, such as a stimulation routine or schedule 130, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit can be programmable. The controller may also terminate a neural stimulation session in response to an interrupt signal, such as may be generated by one or more sensed parameters or any other condition where it is determined to be desirable to stop neural stimulation.

A device may include a programmed therapy schedule or routine stored in memory and may further include a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

According to various embodiments, the stimulation schedule refers to the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2 AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, a particular position/posture, low heart rate levels, and the like. For example, the stimulation can be synchronized to the cardiac cycle based on detected events that enable the stimulation. The therapy schedule can also specify how the stimulation is delivered.

Some embodiments are configured to change a ramp-up time for increasing one or more stimulation parameters from OFF to a programmed intensity at the start of the ON portion. Patients may tolerate higher stimulation levels if there is not an abrupt change at the start of the duty cycle. The parameter increased during this ramp-up time may be amplitude, for example, or other parameter or other combination of parameters that affect the intensity of the stimulation.

Figure 15:
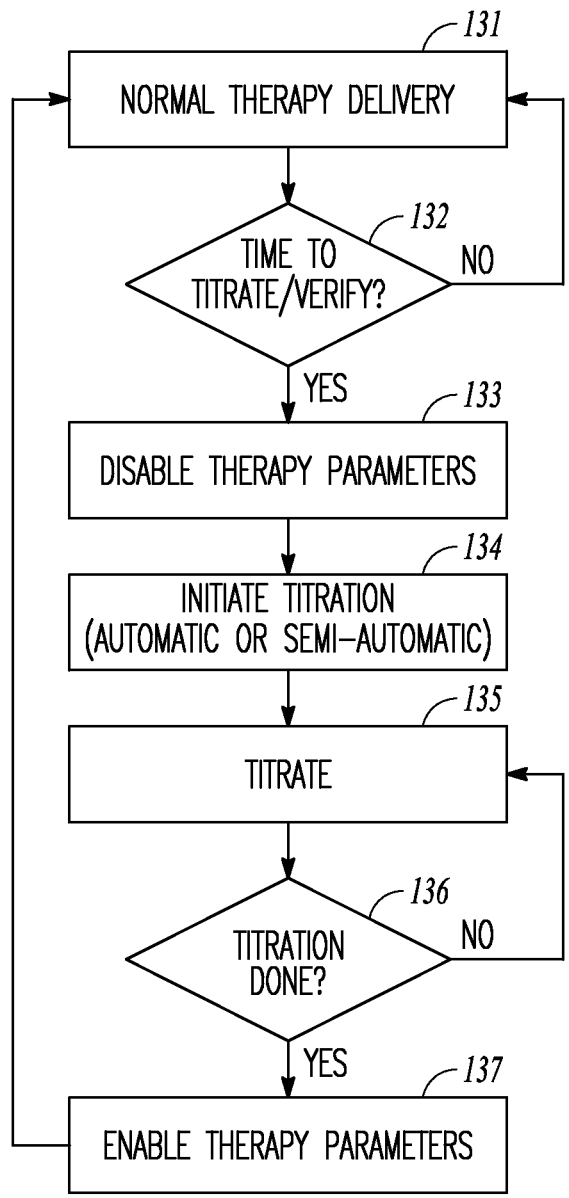
FIG. 15 illustrates an embodiment for titrating stimulation parameters.

FIG. 15 illustrates an embodiment for titrating stimulation parameters. Normal VST is delivered at 131. At 132, it is determined whether it is time to titrate or verify capture. This timing may be based on a schedule, a patient-controlled trigger, a physician-controlled trigger, or a sensed event. If it is determined that it is time to titrate or verify capture, the therapy parameters are disabled at 133 and the titration is initiated at 134. The titration may be automatic or semi-automatic. A titration routine is performed at 135. At 136, it is determined if titration is done. If titration is done, the therapy parameters are enabled at 137. Otherwise, the titration routine continues at 135 until the titration is done.

Figure 16:
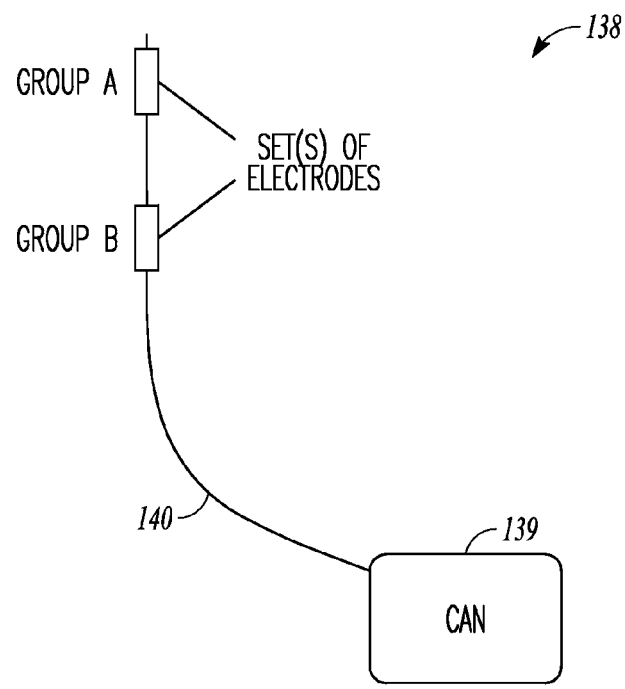
FIG. 16 illustrates an embodiment, by way of example and not limitation, of an implantable medical device with a device housing or can and a lead extending from the can.

FIG. 16 illustrates an embodiment, by way of example and not limitation, of an implantable medical device 138 with a device housing or can 139 and a lead 140 extending from the can. The lead includes multiple poles that can be used in various stimulation configurations including unipolar and bipolar configurations. The lead may be an intravascular lead configured to be fed into position through the vasculature of the patient. The lead may be a subcutaneous lead. The lead may be inside or outside the carotid sheath, to provide electrode(s) either adjacent to or surrounding the vagus nerve. The lead includes at least one group of electrodes to provide the stimulation and recording. The illustrated lead includes two sets of electrodes (Group A and Group B). Each group of electrodes includes one or more electrodes. In some embodiments, the device is configured to switch between different electrode configurations to change stimulation and/or sensing vectors. One group of electrode(s) is used to sense laryngeal muscle activity, and the other group of electrode(s) is used to stimulate the vagus nerve. However, the present subject matter is not limited to a particular number of electrodes or groupings of electrodes. In some embodiments, electrodes from different groups on the leads may be used to provide the desired stimulation/sensing vectors. The can 139 may function as an electrode. In some embodiments, more than one electrode may be on the can 139.

Figure 17:
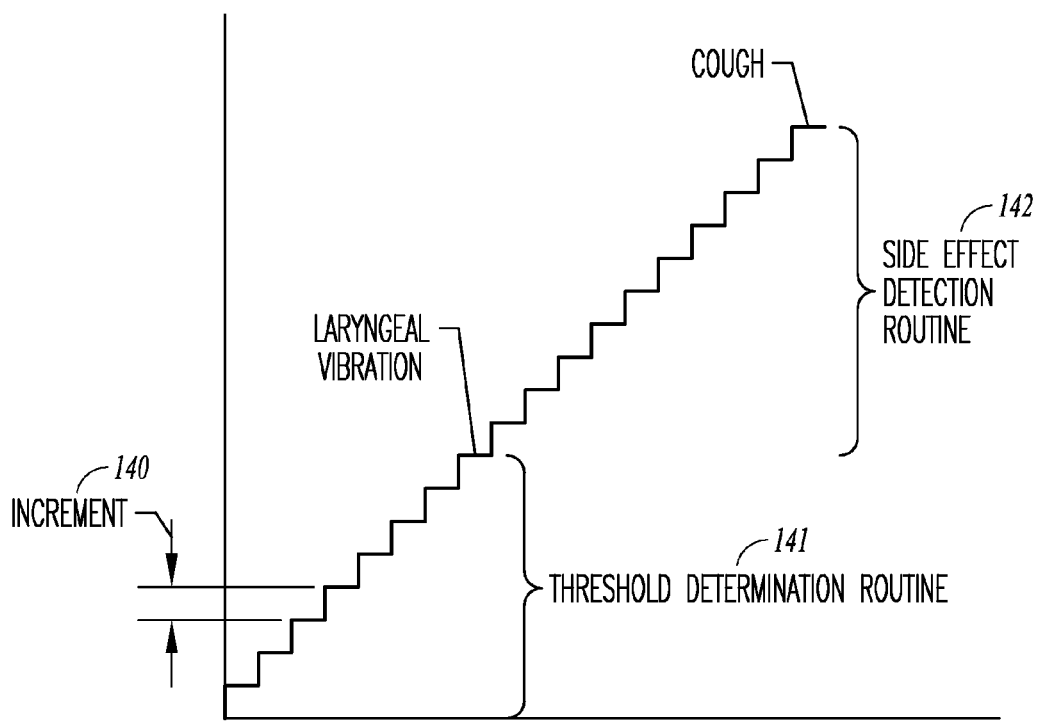
FIG. 17 illustrates an embodiment of a routine for finding threshold values for each of the electrode configurations.

FIG. 17 illustrates an embodiment of a routine for finding threshold values for each of the electrode configurations. The illustrated routine increases the intensity of the neural stimulation therapy over a period of time. The intensity is increased in increments 140. In the illustrated embodiments, a threshold determination routine 141 is performed to detect a lower boundary physiologic response to the neural stimulation such as a laryngeal vibration response. In various embodiments, a side effect detection routine 142 is performed to detect an upper boundary physiologic response (e.g. cough) to the neural stimulation. Some embodiments decrease the intensity of the NCT therapy over a period of time to detect the desired or undesired physiologic responses to the neural stimulation.

Various embodiments detect laryngeal vibration using electromyogram sensors. The laryngeal vibration is a desired physiological response that confirms vagal nerve capture. Some embodiments use sensors to detect an undesired response (e.g. cough or phrenic nerve capture). The sensors may be part of an implantable device, such as an implantable nerve stimulator used to stimulate the target nerve. In some embodiments the sensors are part of a programmer/PSA (pacing system analyzer) or other external system. Some embodiments correlate the timing of the neural stimulation bursts to the timing of the physiological responses to determine whether the physiological response is attributable to the NCT. Some embodiments use feedback from a patient or physician. For example, a clicker pad with a pain assessment or other scale can be used to allow the patient to provide feedback as to whether the stimulation provides cough or phrenic nerve capture or other undesired physiological response to the stimulation. The algorithm can be implemented in the programmer, or in the implantable device, or in an external device configured to communicate with the programmer and/or the implantable device such as in a patient management system.

Some embodiments repeat the algorithm periodically or intermittently, such as may be appropriate to account for lead migration and/or therapy optimization. The system (e.g. device or programmer) may be programmed to initiate the algorithm automatically. In some embodiments, the patient initiates the algorithm using an external device or a signal (e.g. magnet or wireless communication) with the implantable device. In some embodiment the physician or clinician initiates the algorithm.

Figure 18:
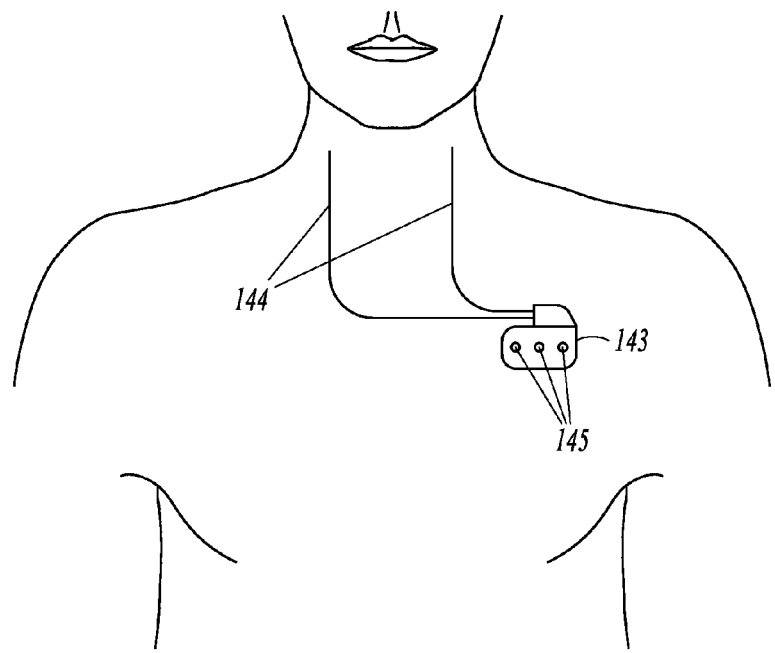
FIG. 18 illustrates a system embodiment in which an implanted medical device (IMD) is placed subcutaneously or submuscularly in a patient's chest with lead(s) positioned to stimulate a vagus nerve.
Figure 19:
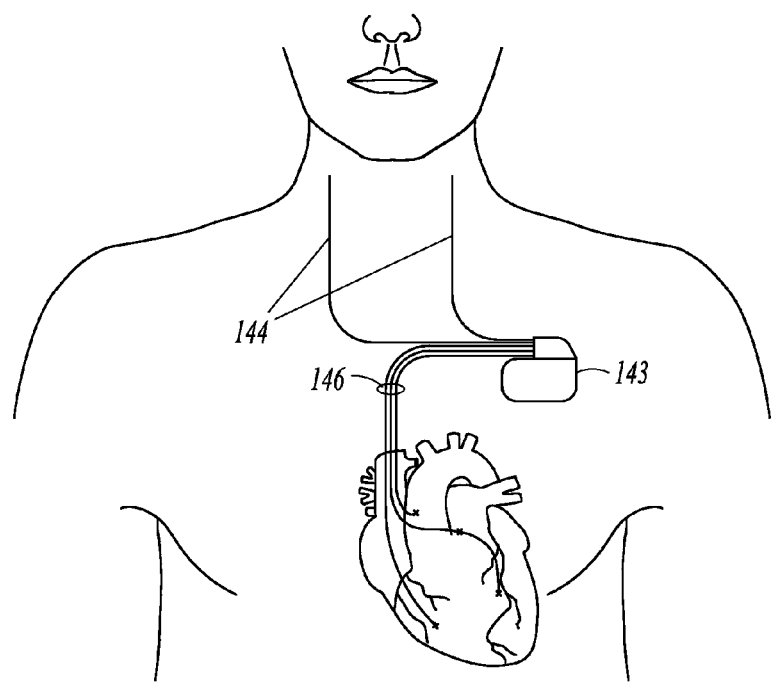
FIG. 19 illustrates an IMD placed subcutaneously or submuscularly in a patient's chest with lead(s) positioned to provide a CRM therapy to a heart, and with lead(s) positioned to stimulate and/or inhibit neural traffic at a vagus nerve, according to various embodiments.

FIGS. 18-19 illustrate system embodiments adapted to provide VST, and are illustrated as bilateral systems that can stimulate both the left and right vagus nerve. The leads can be used to sense EMG signals representing laryngeal muscle activity. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve. FIGS. 18-19 illustrate the use of a lead to stimulate the vagus nerve. Wireless technology could be substituted for the leads, such that a leadless electrode is adapted to stimulate a vagus nerve and is further adapted to wirelessly communicate with an implantable system for use in controlling the VST.

FIG. 18 illustrates a system embodiment in which an IMD 143 is placed subcutaneously or submuscularly in a patient's chest with lead(s) 144 positioned to stimulate a vagus nerve. According to various embodiments, neural stimulation lead(s) 144 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Some embodiments include leadless ECG electrodes 145, such as on the housing of the implantable device as shown in the illustrated system. These ECG electrodes are capable of being used to detect heart rate, for example. FIG. 19 illustrates an IMD 143 placed subcutaneously or submuscularly in a patient's chest with lead(s) 146 positioned to provide a CRM therapy to a heart, and with lead(s) 144 positioned to stimulate and/or inhibit neural traffic at a vagus nerve, according to various embodiments.

Figure 20:
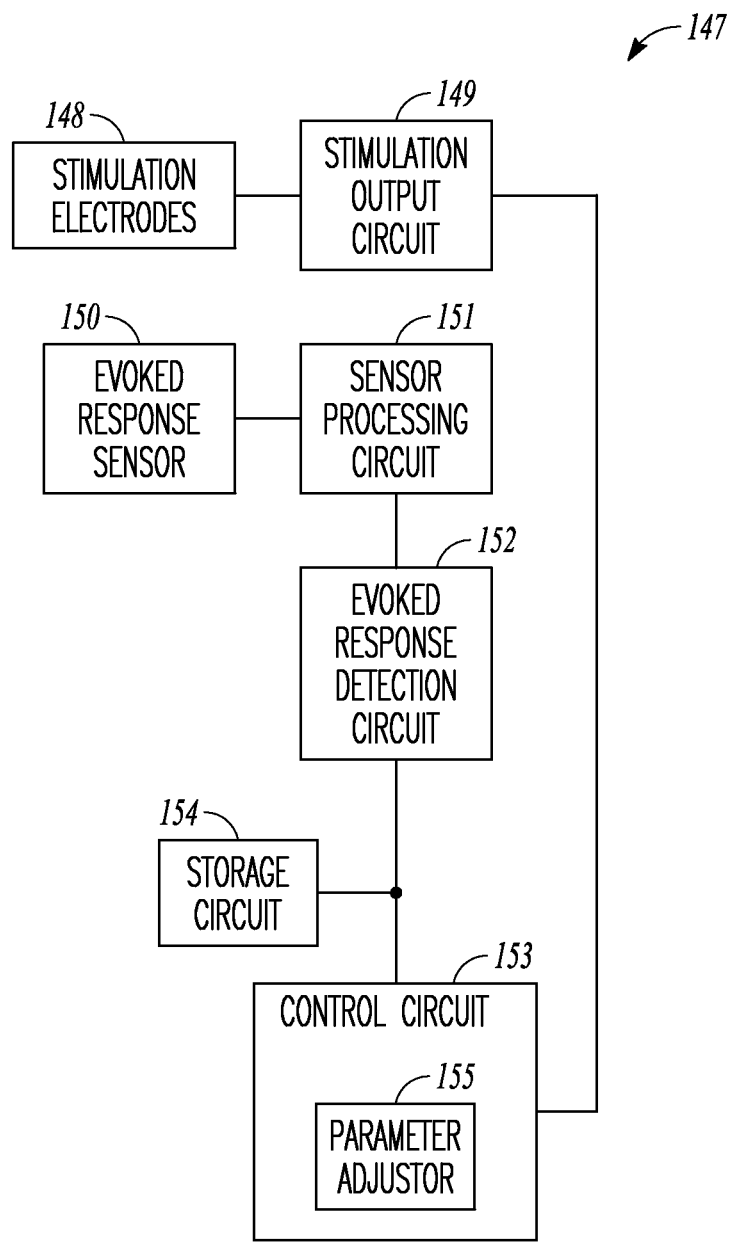
FIGS. 20-21 are block diagrams illustrating embodiments of a vagus nerve stimulation system.

FIG. 20 is a block diagram illustrating an embodiment of a vagus nerve stimulation system 147. The illustrated system 147 includes stimulation electrodes 148, a stimulation output circuit 149, an evoked response sensor 150, a sensor processing circuit 151, an evoked response detection circuit 152, a control circuit 153, and a storage circuit 154. The stimulation electrodes 148 include one or more stimulation electrodes to be placed in the patient's body in one or more locations suitable for delivering neurostimulation pulses to activate a vagus nerve.

The evoked response sensor may include recording electrodes as discussed above. The evoked response sensor 150 is to be placed in or on the patient' body in a location suitable for sensing a physiological signal indicative of evoked responses being physiologic events evoked by the neurostimulation pulses. The evoked response sensor includes a laryngeal activity sensor to sense an evoked muscular response including activities of laryngeal muscle evoked by the neurostimulation pulses. The sensor processing circuit 151 processes the physiological signal in preparation for detection of the evoked responses. The evoked response detection circuit 152 receives the processed physiological signal from sensor processing circuit 151, detects the evoked responses using the processed physiological signal, and generates one or more response signals representative of the detected evoked responses. The one or more response signals includes information about, for example, whether the vagus nerve is captured by the neurostimulation pulses and measured characteristics of the evoked responses. The control circuit 153 controls the delivery of the neurostimulation pulses using a stimulation intensity. The control circuit 153 includes a parameter adjustor 155 to adjust the stimulation intensity by adjusting one or more stimulation parameters (e.g. amplitude, pulse width, or duty cycle). In one embodiment, the parameter adjustor adjusts the one or more stimulation parameters using the one or more response signals generated by the evoked response detection circuit 152. The storage circuit 154, which may be part of or separate from a memory that includes programmed instructions for the device, stores the evoked responses in the form of one or more waveforms of the evoked responses and the one or more characteristic parameters of the evoked responses. In one embodiment, the storage circuit 154 stores the stimulation intensity associated with detected evoked responses. The circuit of system 147 can be programmed to perform the various functions discussed in this document.

Figure 21:
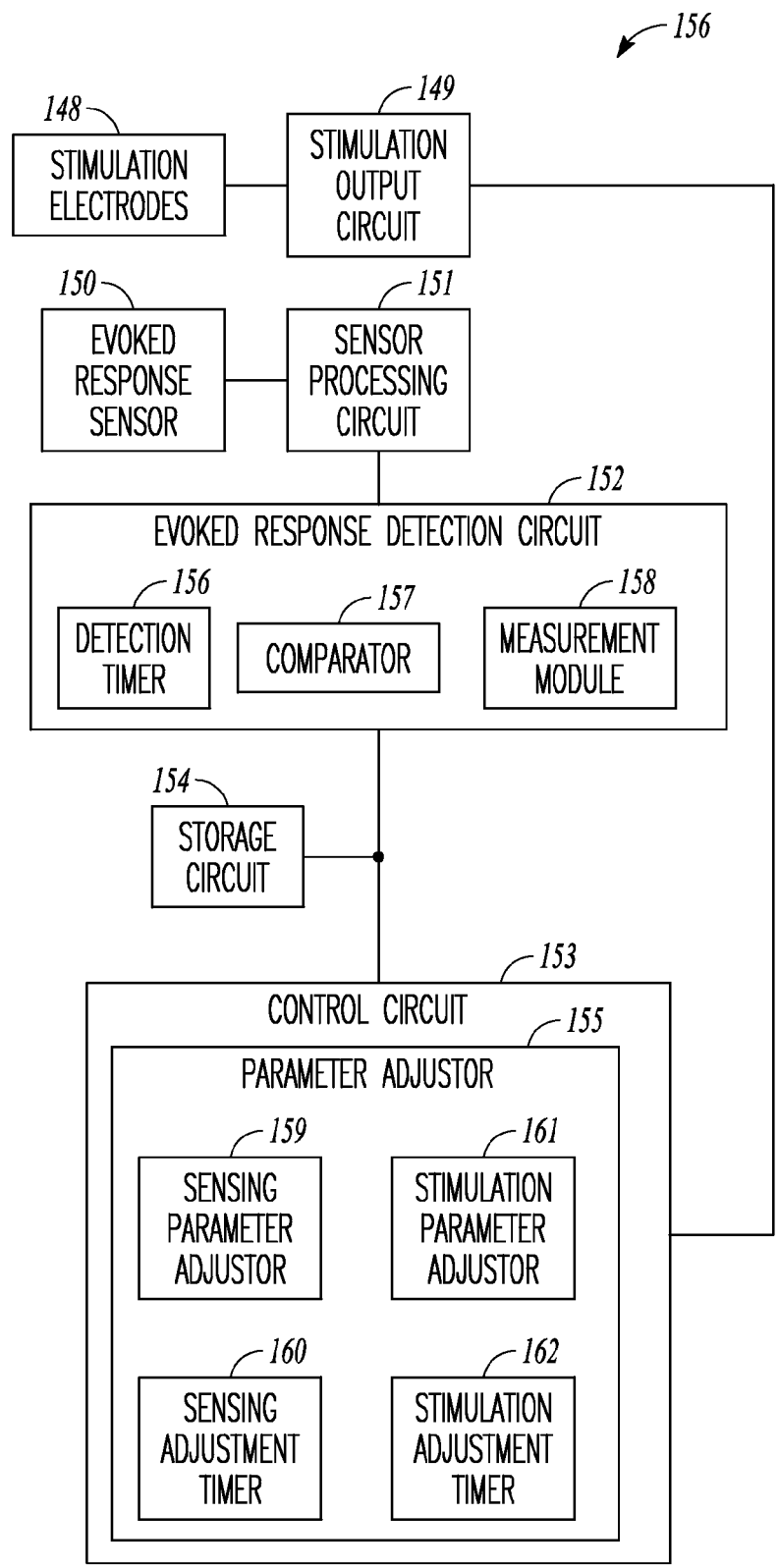

FIG. 21 is a block diagram illustrating an embodiment of a vagus nerve stimulation system 156 that includes stimulation electrodes 148, stimulation output circuit 149, evoked response sensor 150, sensor processing circuit 151, an evoked response detection circuit 152, a control circuit 153, and storage circuit 154.

The evoked response detection circuit 152 detects the evoked responses using the physiological signal and generates one or more response signals representative of the detected evoked responses. The evoked response detection circuit 152 includes a detection timer 156, a comparator 157, and a measurement module 158. The detection timer 156 controls timing of detection of the evoked responses. Examples of such timing include initiation of the detection according to a specified schedule and one or more detection windows within which the evoked responses are expected to be detected. The comparator 157 detects the evoked responses by comparing the physiological signal to one or more detection thresholds. In one embodiment, the comparator 157 detects the evoked responses by comparing the physiological signal to one or more detection thresholds during the one or more detection windows. The measurement module 158 measures one or more characteristic parameters of the evoked responses. Examples of the one or more characteristic parameters include amplitude of the evoked responses, width of the evoked responses, and frequency characteristics of the evoked responses. In various embodiments, the one or more characteristic parameters are each a value measured from one of the evoked responses or being an average of values measured from a plurality of the evoked responses. In various embodiments, examples of the one or more response signals include a capture verification signal declaring capture of the vagus nerve by the neurostimulation pulses and one or more signals representative of the one or more characteristic parameters of the evoked responses.

The control circuit 153 includes a parameter adjustor 155, which adjusts one or more parameters of the stimulation parameters using the one or more response signals. In the illustrated embodiment, the parameter adjustor 155 includes a sensing parameter adjustor 159, a sensing adjustment timer 160, a stimulation parameter adjustor 161, and a stimulation adjustment timer 162. The sensing parameter adjustor 159 adjusts the one or more detection thresholds used by the comparator 157 for detecting the evoked responses. The sensing adjustment timer 160 controls the timing of the adjustment of the one or more detection thresholds according to a specified schedule and/or in response to a user command. The stimulation parameter adjustor 161 adjusts the stimulation intensity by adjusting one or more of the stimulation parameters. Stimulation adjustment timer 162 controls the timing of adjustment of the stimulation intensity according to a specified schedule and/or in response to a user command.

Figure 22:
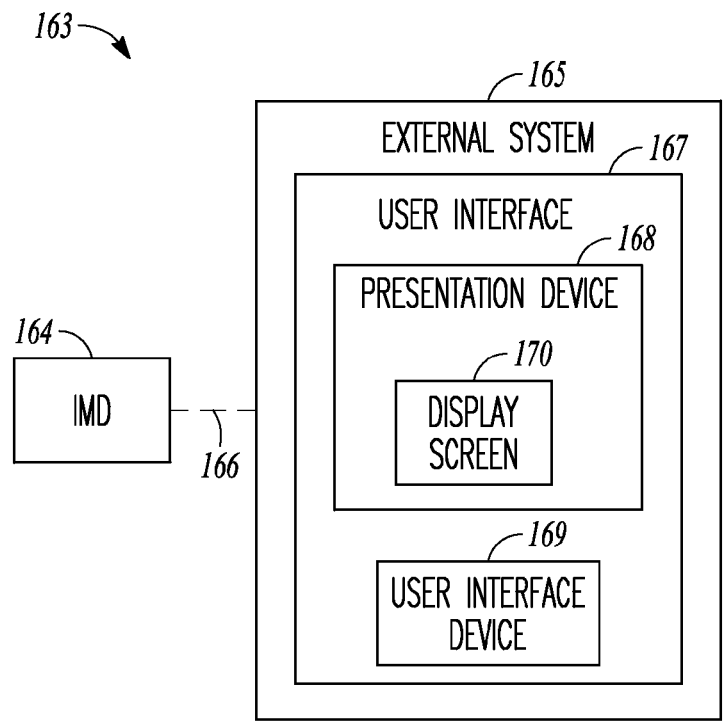
FIG. 22 is a block diagram illustrating an embodiment of an implantable system that includes an IMD and an external system.

FIG. 22 is a block diagram illustrating an embodiment of an implantable system 163. The implantable system 163 includes an IMD 164 and an external system 165. The external system 165 is communicatively coupled to the IMD 164 via telemetry link 166. The external system 165 includes a user interface 167. The user interface 167 includes a presentation device 168 and a user input device 169. The presentation device 168 includes a display screen 170 to display, for example, waveforms of the detected evoked responses, the one or more response signals, the measured one or more characteristics parameters, and/or the stimulation intensity. The user input device 169 receives user commands from a user such as a physician or other caregiver. Examples of the user commands include a user command for starting a delivery of the neurostimulation pulses, a user command to initiate an adjustment of the one or more detection thresholds, a user command to initiate an adjustment of the stimulation intensity, and a user command to initiate automatic capture verification as discussed in this document.

In an embodiment, the external system 165 includes a programmer including user interface 167. In an embodiment, external system 165 includes a patient management system including an external device communicatively coupled to IMD 164 via telemetry link 166 and a remote device in a distant location and communicatively coupled to the external device via a communication network. The external device and/or the remote device include the user interface 167.

Figure 23:
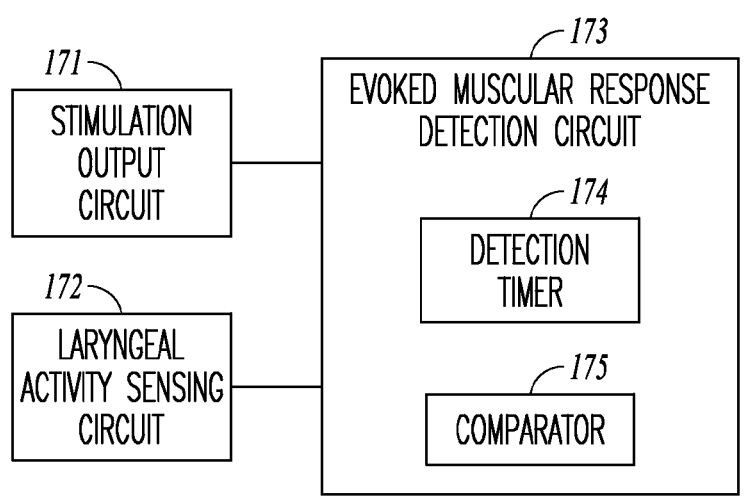
FIG. 23 is a block diagram illustrating an embodiment of a circuit for detecting evoked muscular responses.

FIG. 23 is a block diagram illustrating an embodiment of a circuit for detecting evoked muscular responses. In one embodiment, the circuit is included in an IMD. The circuit includes stimulation output circuit 171, a laryngeal activity sensing circuit 172, and an evoked muscular response detection circuit 173. The stimulation output circuit 171 delivers neurostimulation pulses to the vagus nerve. The laryngeal activity sensing circuit 172 senses a laryngeal signal representative of activities of the laryngeal muscle including evoked muscular responses each evoked by one of the neurostimulation pulses. The evoked muscular response detection circuit 173 detects the evoked muscular responses using the laryngeal signal. In the illustrated embodiment, evoked neural response detection circuit 173 includes a detection timer 174 and a comparator 175. The detection timer 174 times a detection window during which the detection of an evoked muscular response is anticipated. The comparator 175 detects the evoked muscular responses by comparing the sensed laryngeal signal to one or more detection thresholds during the detection window.

Figure 24:
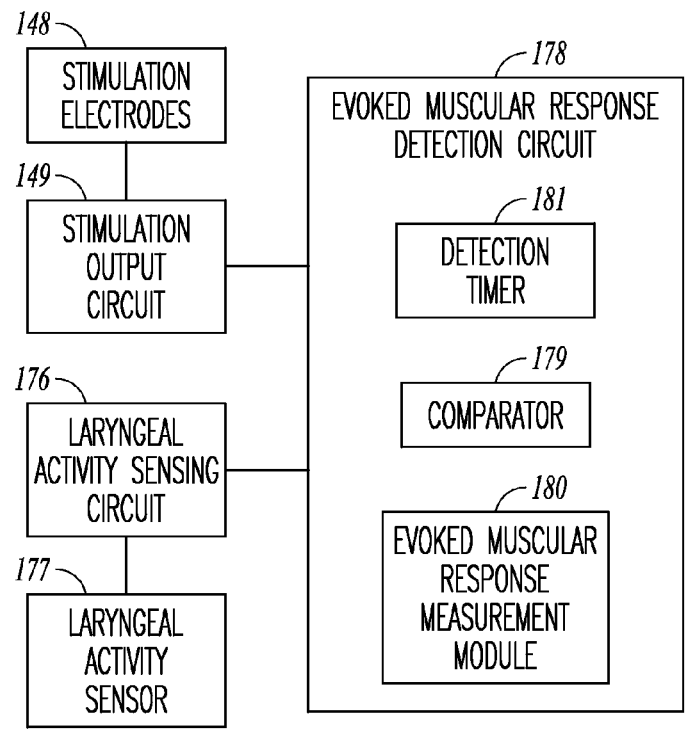
FIG. 24 is a block diagram illustrating an embodiment of a system for detecting evoked muscular responses.

FIG. 24 is a block diagram illustrating an embodiment of a system for detecting evoked muscular responses. The system includes stimulation electrodes 148, stimulation output circuit 149, a laryngeal activity sensor 176, a laryngeal activity sensing circuit 177, and an evoked muscular response detection circuit 178.

The evoked muscular response detection circuit 178 detects the evoked muscular responses using the sensed laryngeal signal. The evoked muscular response detection circuit 178 includes comparator 179 and an evoked muscular response measurement module 180, and includes a detection timer 181 if the detection window is used. In one embodiment, the evoked muscular response detection circuit 178 detects the evoked muscular response according to a specified schedule, such as on a periodic basis, or in response to a user command. The evoked muscular response measurement module 180 measures one or more characteristic parameters. In one embodiment, evoked muscular response measurement module 180 measures and trends the one or more characteristic parameters. Examples of the one or more characteristic parameters include the amplitude of an evoked muscular response, the sum of multiple evoked muscular responses that follow multiple neurostimulation pulses, and the time between the delivery of a neurostimulation pulse and the detection of the evoked muscular response resulting from the delivery of that neurostimulation pulse. The amplitude of the evoked muscular responses increases as more motor fibers (A-fibers) are captured by delivery of the neurostimulation pulses. More motor fibers are captured as the stimulation intensity increases.

Figure 25:
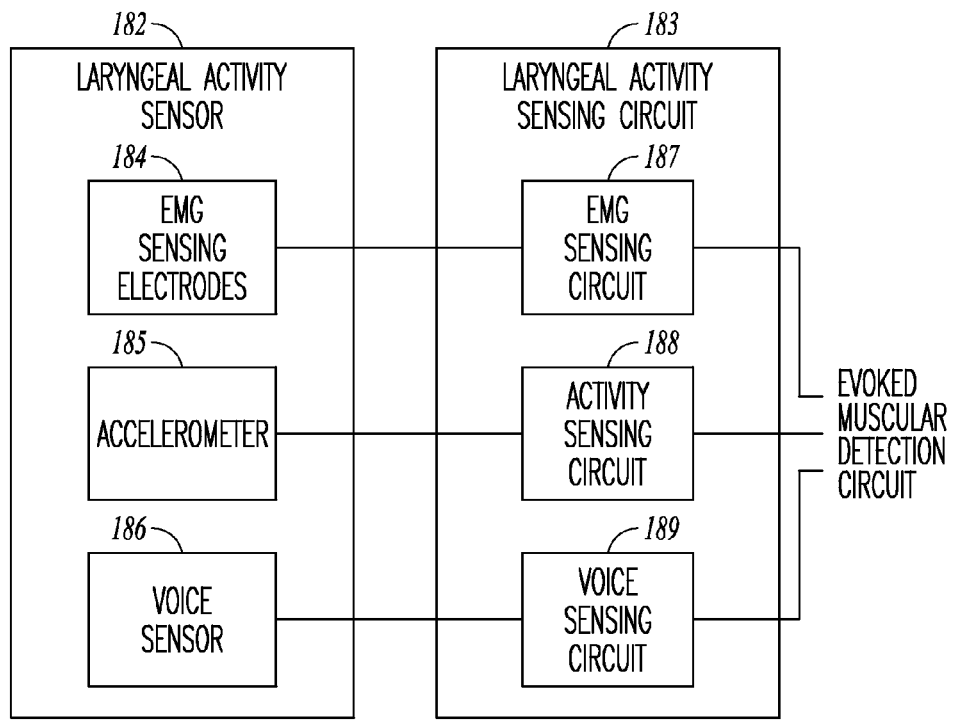
FIG. 25 is a block diagram illustrating an embodiment of a circuit for sensing various laryngeal signals.

FIG. 25 is a block diagram illustrating an embodiment of a circuit for sensing various laryngeal signals. The circuit includes a laryngeal activity sensor 182 and a laryngeal activity sensing circuit 183. In the illustrated embodiment, laryngeal activity sensor 182 includes EMG sensing electrodes 184, and may further include an accelerometer 185, a voice sensor 186, and a laryngeal activity sensing circuit 183 that includes an EMG sensing circuit 187, and may further include an activity sensing circuit 188, and a voice sensing circuit 189. This allows for selection of a laryngeal signal by the user or the system, and also allows for use of multiple laryngeal signals for the detection of the evoked muscular responses. The EMG sensing circuit 187 senses the EMG signal through EMG sensing electrodes 184. The evoked muscular response detection circuit detects the evoked muscular responses using the sensed EMG signal.

The accelerometer 185 may be configured to be placed in or on the patient's body in a location suitable for sensing an acceleration signal as the laryngeal signal. The acceleration signal is indicative of activities of the laryngeal muscle including the evoked muscular responses. In one embodiment, the accelerometer 185 includes an implantable accelerometer. The activity sensing circuit 188 processes the acceleration signal sensed by the accelerometer 185. The evoked muscular response detection circuit detects the evoked muscular responses using the processed acceleration signal.

The voice sensor 186 is configured to be placed in or on the patient's body in a location suitable for sensing a voice signal as the laryngeal signal. Vagus nerve stimulation is known to cause change in a patient's voice, such as hoarseness, by activating the laryngeal muscle. Thus, certain changes in the voice signal are indicative of activities of the laryngeal muscle including the evoked neuromuscular responses. The voice sensing circuit 189 processes the voice signal sensed by voice sensor 186. The evoked muscular response detection circuit detects the evoked muscular responses using the processed voice signal, such as by detecting changes in frequency characteristics of the voice signal.

Figure 26:
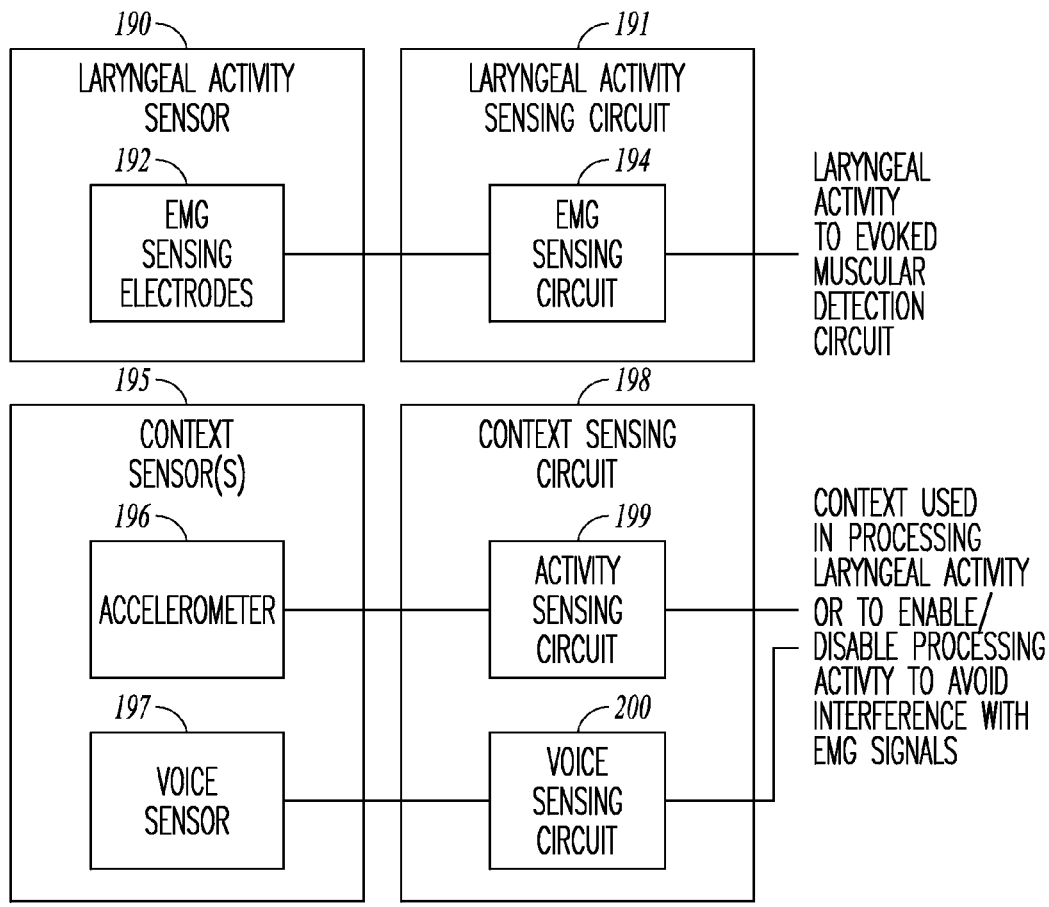
FIG. 26 is a block diagram illustrating an embodiment of a circuit for sensing various laryngeal signals in context.

FIG. 26 is a block diagram illustrating an embodiment of a circuit for sensing various laryngeal signals in context. The circuit includes a laryngeal activity sensor 190 and a laryngeal activity sensing circuit 191. In the illustrated embodiment, the laryngeal activity sensor 190 includes EMG sensing electrodes 192 and the laryngeal activity sensing circuit 191 includes an EMG sensing circuit 194. The output of the laryngeal activity sensing circuit 191 is a signal representative of the laryngeal activity. The circuit further includes context sensor(s) 195 such as an accelerometer 196 or a voice sensor 197, and further includes context sensing circuit 198 such as an activity sensing circuit 199, and a voice sensing circuit 200. The output of the context sensing circuit can be used to override the processing of the laryngeal activity signal. For example, a vagus nerve capture routine or a titration routine may not be enabled if the context sensing circuit detects activity or detects the patient's voice, both of which may adversely interfere with the EMG sensing of laryngeal activity. In embodiments in which the laryngeal activity is stored for later processing, the associated context can also be stored with the laryngeal activity. The use of this context information can be used to avoid interference from other muscle activity that is not attributable to vagus nerve stimulation.

Figure 27:
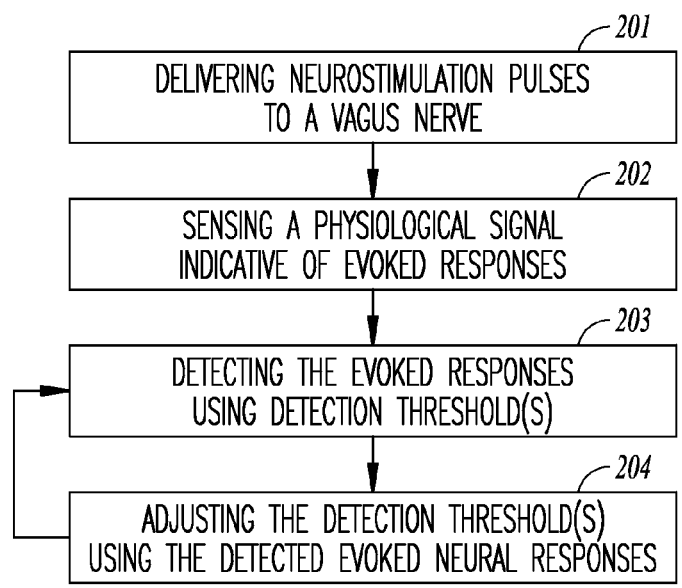
FIG. 27 is a flow chart illustrating an embodiment of a method for automatic threshold adjustment (also referred to as "Auto-Sense") for evoked response detection during vagus nerve stimulation.

FIG. 27 is a flow chart illustrating an embodiment of a method for automatic threshold adjustment (also referred to as "Auto-Sense") for evoked response detection during vagus nerve stimulation. In various embodiments, the evoked response detection circuit is configured to perform the method according to a specified schedule. In one embodiment, the evoked response detection circuit may be configured to perform the method periodically or in response to an event, such as monthly, weekly, daily, hourly, once each burst of the neurostimulation pulses, or once each pulse of the neurostimulation pulses.

At 201, neurostimulation pulses are delivered to a vagus nerve. At 202, the laryngeal signal is sensed. At 203, the evoked muscular responses are detected. In one embodiment, an evoked muscular response waveform representative of the evoked muscular responses is detected and stored. The waveform is of one detected evoked muscular response or an average of several detected evoked muscular responses. In one embodiment, one or more characteristic parameters of the evoked muscular responses are measured. Examples of the one or more characteristic parameters include a maximum amplitude of the sensed laryngeal signal. In one embodiment, the measured one or more characteristic parameters are trended and/or stored for presentation to the user as scheduled or needed. At 204, the one or more detection thresholds are adjusted using the detected evoked muscular responses. In one embodiment, the detected evoked muscular responses are compared to a stored baseline response. This includes comparing the evoked response waveform to a stored baseline waveform and/or comparing the one or more characteristic parameters to the stored one or more baseline characteristic parameters. The baseline waveform and/or the one or more baseline characteristic parameters are established for a patient during the initial system setup for the patient (such as implantation of an implantable system), during a follow-up visit, or automatically by an evoked muscular response detection circuit when certain criteria are met. At 204, the one or more detection thresholds are adjusted in response to the detected evoked muscular responses substantially deviating from the stored baseline response. In one embodiment, the user is alerted in response to the detected evoked muscular responses substantially deviating from the stored baseline response.

Figure 28:
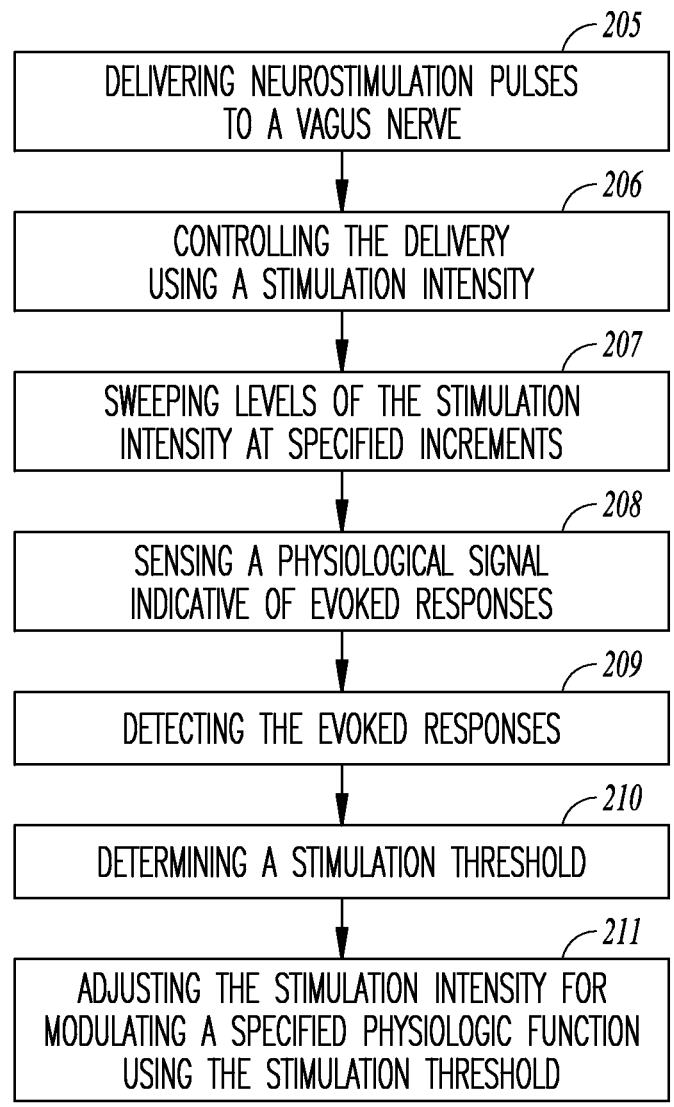
FIG. 28 is a flow chart illustrating an embodiment of a method for adjusting stimulation intensity for vagus nerve stimulation.

FIG. 28 is a flow chart illustrating an embodiment of a method for adjusting stimulation intensity for vagus nerve stimulation. At 205, neurostimulation pulses are delivered to a vagus nerve. At 206, the delivery of the neurostimulation pulses is controlled using a stimulation intensity. The stimulation intensity is adjustable by adjusting stimulation parameters. At 207, the stimulation intensity is swept at specified increments. At 208, an EMG sensor is used to sense activity of laryngeal muscles. At 209, the sensed activity of the laryngeal muscles is used to detect activity of the laryngeal muscles. At 210, a stimulation threshold is determined. The stimulation threshold is a minimum level of the stimulation intensity for providing the detected activity of the laryngeal muscles. At 211, the stimulation intensity is adjusted for modulating a specified physiologic function using the stimulation threshold. In one embodiment, the physiologic function includes a cardiovascular function. In an embodiment, the stimulation threshold is trended and used to indicate pathological conditions and/or device problems. For example, a substantially increasing stimulation threshold may indicate device problems such as poor electrical connections or lead failure or pathological conditions such as nerve damage. When this happens, the user is alerted for examining the patient and the neurostimulation system. If the stimulation threshold is not determined after the stimulation intensity is swept through its maximum level, the user is also alerted because an abnormally high stimulation threshold is indicative of the device problems or pathological conditions. The laryngeal signal is detected at 208 and the evoked muscular responses are detected at 209. An evoked muscular response waveform representative of the evoked muscular responses may be detected and stored. The waveform may be one detected evoked muscular response or an average of several detected evoked muscular responses. With reference to 210, the stimulation threshold for one or more specified effects in the evoked muscular response is determined. Examples of the one or more specified effects include that the amplitude of the sensed laryngeal signal during a detection window reaches a threshold amplitude, that an evoked muscular response is detected during the detection window, and a correlation between the detected evoked muscular response waveform and a stored baseline waveform reaches a threshold correlation.

Figure 29:
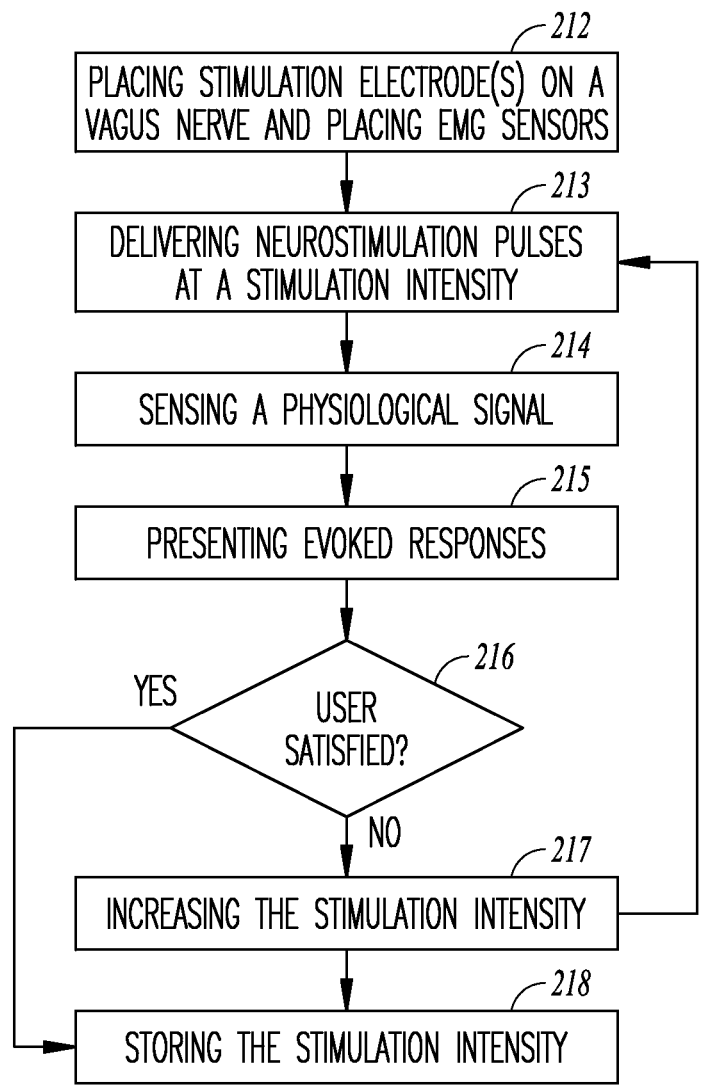
FIG. 29 is a flow chart illustrating an embodiment of a method for adjusting stimulation intensity for vagus nerve stimulation during implantation of an implantable medical device.

FIG. 29 is a flow chart illustrating an embodiment of a method for adjusting stimulation intensity for vagus nerve stimulation during implantation of an implantable medical device. At 212, a lead is implanted with stimulation electrodes on or near a vagus nerve for stimulating the vagus nerve of a patient and with EMG sensor(s) for sensing laryngeal activity. The stimulation electrodes are connected to a neurostimulator including a stimulation output circuit and a control circuit for delivering neurostimulation pulses to the vagus nerve. The neurostimulator may be an external device for use during the implantable procedure or the implantable medical device intended to be implanted into the patient. At 213, the neurostimulation pulses are delivered through the stimulation electrodes. The delivery of the neurostimulation pulses is controlled using a stimulation intensity that starts at a specified low level. The stimulation intensity is controlled by one or more stimulation parameters. At 214, the physiological signal is sensed. At 215, the evoked responses, including waveforms and measured information, are presented to the user on a display screen. Examples of the presented information include the amplitude of the evoked muscular responses, the sum of a plurality of the evoked muscular responses, the time between the delivery of a neurostimulation pulse and the detection of the evoked muscular response resulting from the delivery of that neurostimulation pulse, and the stimulation parameters including those controlling the stimulation intensity. At 217, if the user is not satisfied with the evoked neural responses at 216, the stimulation intensity is increased by increasing the pulse amplitude and/or the pulse width. If the stimulation intensity cannot be further increased, the user is alerted for examining the patient for possible pathological conditions preventing effectiveness of the neurostimulation and/or the system for possible device and/or connection problems. At 218, if the user is satisfied with the evoked neural responses associated with a level of the stimulation intensity at 216, that level of the stimulation intensity is stored and used to determine the subsequent vagus nerve stimulation therapy delivered from the implantable medical device.

Figure 30:
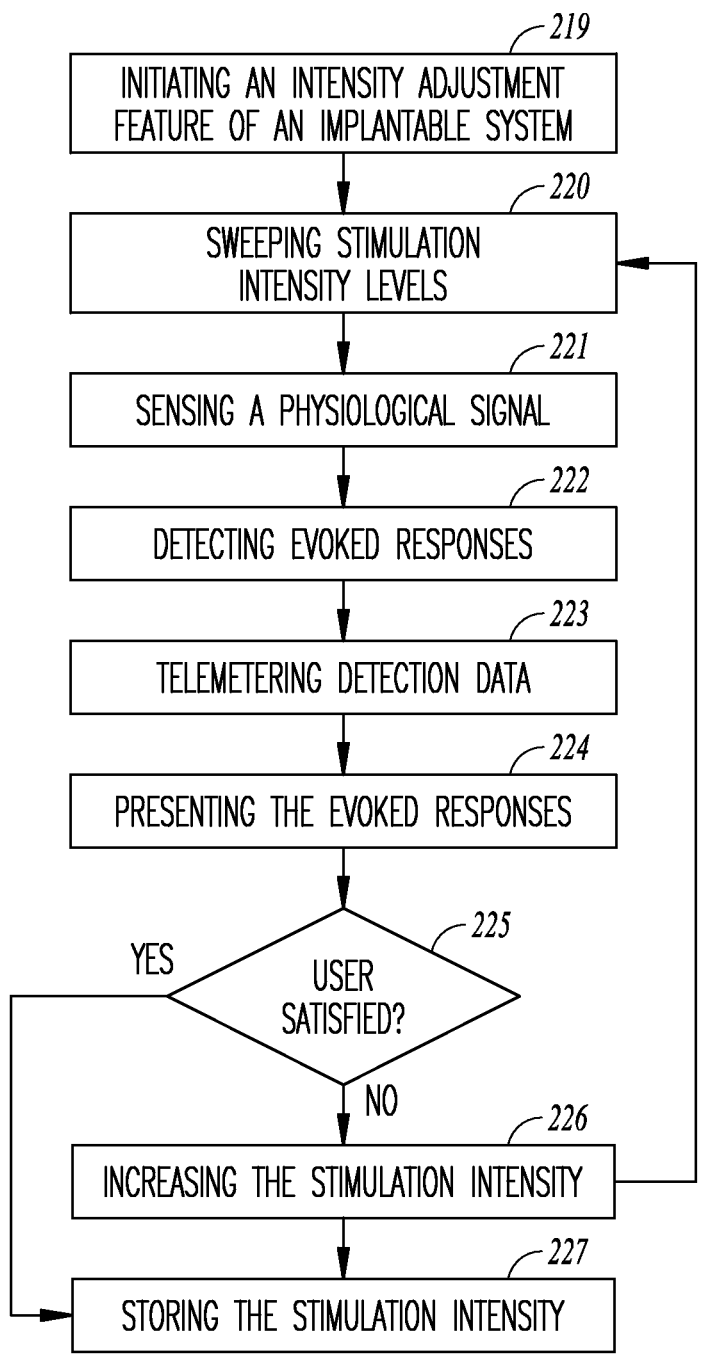
FIG. 30 is a flow chart illustrating an embodiment of a method for adjusting stimulation intensity for vagus nerve stimulation during follow-up visits by the patient using the implantable medical device.

FIG. 30 is a flow chart illustrating an embodiment of a method for adjusting stimulation intensity for vagus nerve stimulation during follow-up visits by the patient using the implantable medical device. At 219, an intensity adjustment feature of the implantable medical device is initiated by the user. In one embodiment, a stimulation adjustment timer initiates the adjustment of stimulation intensity in response to a user command entered by the user using an external system communicatively coupled to the implantable medical device. At 220, stimulation intensity levels are swept. This includes incrementally increasing the pulse amplitude and/or the pulse width from specified low values. At 221, the laryngeal signal is sensed using the EMG sensor that was implanted in the patient with the stimulation electrodes. At 222, the evoked laryngeal muscular responses are detected. At 223, data representative of the detected evoked responses are telemetered to the external system. At 224, the evoked responses, including waveforms and measured information, are presented to the user on a display screen of the external system using the telemetered data. When the physiological signal includes the laryngeal signal, examples of the presented information include the amplitude of the evoked muscular responses, the sum of a plurality of the evoked muscular responses, the time between the delivery of a neurostimulation pulse and the detection of the evoked muscular response resulting from the delivery of that neurostimulation pulse, and stimulation parameters including those controlling the stimulation intensity. At 226, if the user is not satisfied with the evoked neural responses at 225, the stimulation intensity is increased by increasing the pulse amplitude and/or the pulse width. If the stimulation intensity cannot be further increased, the user is alerted for examining the patient for possible pathological conditions preventing effectiveness of the neurostimulation and/or the system for possible device and/or connection problems. At 227, if the user is satisfied with the evoked neural responses associated with a level of the stimulation intensity at 225, that level of the stimulation intensity (in terms of the pulse amplitude and the pulse width) is stored and used to determine the subsequent vagus nerve stimulation therapy delivered from the implantable medical device.

Figure 31:
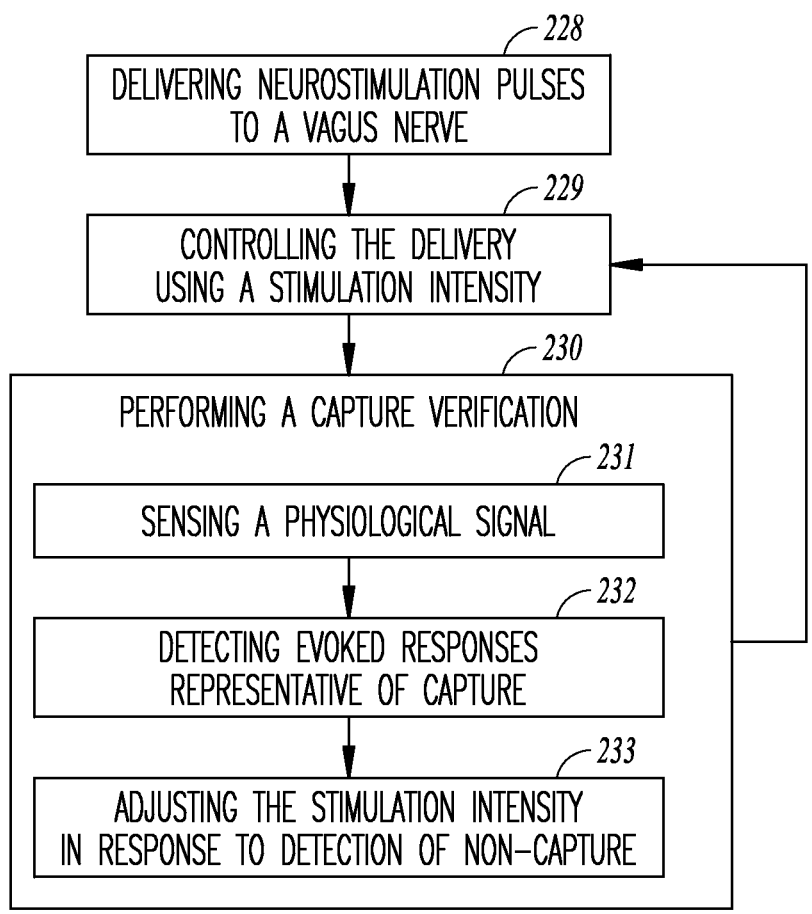
FIG. 31 is a flow chart illustrating an embodiment of a method for automatic capture verification (also referred to as "Auto-Capture") for vagus nerve stimulation.

FIG. 31 is a flow chart illustrating an embodiment of a method for automatic capture verification (also referred to as "Auto-Capture") for vagus nerve stimulation. The automatic capture verification provides automatic verification of capture of the vagus nerve by neurostimulation pulses and adjustment of the stimulation intensity. The control circuit may be configured to perform the automatic capture verification according to a schedule or periodically or according to an event, such as monthly, weekly, daily, hourly, once each burst of the neurostimulation pulses, or once each pulse of the neurostimulation pulses. At 228, neurostimulation pulses are delivered to a vagus nerve. At 229, the delivery of the neurostimulation pulses is controlled using a stimulation intensity. The stimulation intensity is adjusted by adjusting stimulation parameters. At 230, a capture verification is performed. At 231, the laryngeal signal is sensed. At 232, one of the evoked muscular responses for each pulse of the neurostimulation pulses delivered is detected. At 233, the stimulation intensity is adjusted in response to a specified one or more of the evoked muscular responses not detected (i.e. non-capture) for a specified number of the neurostimulation pulses delivered. In one embodiment, the stimulation intensity is adjusted in response to an evoked muscular response not being detected for one of the neurostimulation pulses delivered. In another embodiment, the stimulation intensity is adjusted in response to the evoked muscular response not being detected for a specified first number of the neurostimulation pulses delivered out of a specified second number of the neurostimulation pulses delivered. In another embodiment, the stimulation intensity is adjusted in response to an evoked muscular response not being detected for a rolling average number of the neurostimulation pulses delivered. The stimulation intensity may be lowered to prevent unnecessary energy delivered with the neurostimulation pulses to promote device longevity. If an unacceptable degree of loss of capture occurs when the stimulation intensity is set to about the available maximum level, the user is alerted for examining the patient for possible pathological conditions preventing effectiveness of neurostimulation and/or the system for possible device and/or connection problems.

In one embodiment, each of the automatic threshold adjustment (Auto-Sense), automatic stimulation intensity adjustment (Auto-Threshold), and automatic capture verification (Auto-Capture) is disabled or delayed if noise in the sensed physiological signal exceeds a specified threshold noise level, due to the patient's activities and speeches for example. In one embodiment, each of the automatic threshold adjustment (Auto-Sense), automatic stimulation intensity adjustment (Auto-Threshold), and automatic capture verification (Auto-Capture) is performed with various parameters such as the detection thresholds adjusted for the patient's posture, activity level and voice.

As will be understood by one of ordinary skill in the art upon reading and comprehending the present subject matter, various embodiments of the present subject matter improve the ability to quickly and accurately implant and program a neural stimulation system and intermittently reprogram the system, improve patient acceptance of therapy and maintain efficacious levels of therapy. The modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for detecting vagus nerve capture using an implanted lead, comprising:
   delivering neurostimulation pulses through the lead to a vagus nerve;
   sensing EMG signals from laryngeal muscle activity using the lead; and
   detecting evoked laryngeal muscle activity evoked by the neurostimulation pulses using the sensed EMG signals.

2. The method of claim 1, wherein the lead includes a vagal nerve cuff, and wherein sensing EMG signals includes sensing EMG signals from laryngeal muscle activity using electrodes on the vagal nerve cuff.

3. The method of claim 2, wherein delivering neurostimulation pulses includes delivering neurostimulation pulses to the vagus nerve using the electrodes on the vagal nerve cuff.

4. The method of claim 1, wherein the lead is configured to be intravascularly inserted into an internal jugular vein, and wherein delivering neurostimulation pulses includes transvascularly stimulating the vagus nerve using the lead in the internal jugular vein, and sensing EMG signals from laryngeal activity includes using the lead in the internal jugular vein to sense EMG signals.

5. The method of claim 1, wherein the lead has a first set of electrodes and a second set of electrodes, and the first set of electrodes is proximate to a distal end of the lead, wherein sensing EMG signals from laryngeal activity includes using the first set of electrodes to sense EMG signals from laryngeal muscle activity, and delivering neurostimulation pulses includes using the second set of electrodes to deliver neurostimulation pulses to the vagus nerve through the lead.

6. The method of claim 1, wherein the lead is configured to be implanted extravascularly within a carotid sheath, wherein delivering neural stimulation includes using the lead implanted extravascularly within the carotid sheath to stimulate the vagus nerve, and sensing EMG signals from laryngeal activity includes using the lead implanted extravascularly within the carotid sheath to sense EMG signals from laryngeal activity.

7. The method of claim 1, wherein:
the lead has a first set of electrodes and a second set of electrodes, wherein the first set of electrodes is proximate to a distal end of the lead and, when implanted, the second set of electrodes is more caudal than the first set of electrodes and is more cranial than a point where the recurrent laryngeal nerve branches from the vagus nerve;
sensing EMG signals from laryngeal activity includes using the first set of electrodes to sense EMG signals from laryngeal muscle activity; and
delivering neural stimulation pulses includes using the second set of electrodes to deliver neurostimulation pulses to the vagus nerve through the lead.

8. The system of claim 1, further comprising:
timing a delay interval after delivery of one of the neurostimulation pulses, and timing a detection window starting upon expiration of the delay interval; and
detecting the evoked laryngeal muscle activity by comparing the sensed EMG signals within the detection window to a template or by comparing a value derived from the sensed EMG signals within the detection window to a threshold value.

9. The method of claim 8, wherein the detection window begins about 8 ms and ends about 12 ms after delivery of one of the stimulation pulses.

10. The method of claim 8, wherein detecting the evoked laryngeal muscle activity includes comparing the sensed EMG signals to a patient-specific template.

11. The method of claim 8, further comprising generating an active recharge pulse after each neurostimulation pulse, and completing the active recharge pulse during the time delay interval.

12. The method of claim 8, further comprising generating a passive recharge after each neurostimulation pulse, interrupting the passive recharge during the detection window, and resuming the passive recharge after completion of the detection window.

13. The method of claim 1, further comprising measuring one or more characteristic parameters of the evoked laryngeal muscle activity and generating a signal representative of the one or more characteristic parameters.

14. The method of claim 1, enabling detection of the evoked laryngeal muscle activity according to a programmed schedule.

15. The method of claim 1, further comprising enabling detection of the evoked laryngeal muscle activity in response to a physician-initiated command signal.

16. The method of claim 1, further comprising enabling detection of the evoked laryngeal muscle activity in response to a patient-initiated command signal.

17. The method of claim 1, further comprising detecting an event, and automatically enabling detection of the evoked laryngeal muscle activity in response to detecting the event.

18. The method of claim 1, further comprising sensing context to provide a contextual signal, and using the contextual signal and the sensed EMG signals to detect evoked laryngeal muscle activity evoked by the neurostimulation pulses.

19. The method of claim 1, further comprising automatically adjusting a parameter of the neurostimulation pulses, using a control circuit, to evoke desired laryngeal muscle activity.

20. The method of claim 1, wherein the method is performed by an implanted medical device.

* * * * *